(12) United States Patent
Wörle et al.

(10) Patent No.: US 9,522,377 B2
(45) Date of Patent: *Dec. 20, 2016

(54) METHOD FOR IMPROVING THE PROPERTIES OF AMPHIPHILE PARTICLES

(75) Inventors: Gert Wörle, Bielefeld (DE); Fredrik Tiberg, Lund (SE); Markus Johnsson, Lund (SE); Heike Bunjes, Jena (DE); Britta Siekmann, Lomma (SE); Justas Barauskas, Lund (SE)

(73) Assignee: CAMURUS AB, Lund (SE)

(*) Notice: Subject to any disclaimer, the term of this patent is extended or adjusted under 35 U.S.C. 154(b) by 2105 days.

This patent is subject to a terminal disclaimer.

(21) Appl. No.: 10/566,972

(22) PCT Filed: Aug. 4, 2004

(86) PCT No.: PCT/GB2004/003387
§ 371 (c)(1),
(2), (4) Date: Nov. 27, 2006

(87) PCT Pub. No.: WO2005/014162
PCT Pub. Date: Feb. 17, 2005

(65) Prior Publication Data
US 2007/0134336 A1    Jun. 14, 2007

(30) Foreign Application Priority Data

Aug. 4, 2003  (GB) .................. 0318244.1
Sep. 23, 2003 (GB) .................. 0322279.1
(Continued)

(51) Int. Cl.
*B01J 13/02* (2006.01)
*A61K 9/50* (2006.01)
*B01J 13/00* (2006.01)

(52) U.S. Cl.
CPC .............. *B01J 13/02* (2013.01); *A61K 9/5089* (2013.01); *B01J 13/00* (2013.01)

(58) Field of Classification Search
CPC .......... B01J 13/00; B01J 13/02; A61K 9/5089; A61K 9/50; A61K 9/501
(Continued)

(56) References Cited

U.S. PATENT DOCUMENTS 5,055,228 A    10/1991  Handjani et al.
5,531,925 A *   7/1996  Landh et al. ............... 516/56
(Continued)

FOREIGN PATENT DOCUMENTS

GB    1 539 625    1/1979
WO    99/12640     3/1999

OTHER PUBLICATIONS

Koynova et al, Modulation of lipid phase behavior by kosmotropic and chaotropic solutes Experiment and thermodynamic theory, European Biophysics, Mar. 1997, 25, 261-274.*
(Continued)

Primary Examiner — Daniel S Metzmaier
(74) Attorney, Agent, or Firm — Nixon & Vanderhye P.C.

(57) ABSTRACT

The present invention provides a method for forming a dispersion comprising non-lamellar amphiphile particles having improved phase behavior, particle size distribution and/or storage stability, said method comprising forming a dispersion of lamellar and optionally non-lamellar particles comprising at least one structuring agent in a polar solvent, heating said particles to an elevated temperature, followed by cooling, wherein said heating is to a temperature and for a period sufficient to provide, after cooling, a measurable improvement in phase behavior, particle size distribution and/or storage stability.

11 Claims, 13 Drawing Sheets

(30) Foreign Application Priority Data

Jan. 23, 2004 (GB) .................................. 0401514.5
Jun. 7, 2004 (GB) .................................. 0412671.0

(58) Field of Classification Search
USPC ........................................... 516/77; 424/489
See application file for complete search history.

(56) References Cited

U.S. PATENT DOCUMENTS

| | | | | |
|---|---|---|---|---|
| 5,670,099 A | * | 9/1997 | Morancais et al. | 264/4.3 |
| 6,066,328 A | | 5/2000 | Somonnet et al. | |
| 6,482,517 B1 | * | 11/2002 | Anderson | 428/402.24 |
| 8,236,292 B2 | * | 8/2012 | Thuresson et al. | 424/85.7 |
| 9,067,190 B2 | * | 6/2015 | Joabsson | B01J 13/00 |
| 2003/0232340 A1 | * | 12/2003 | Anderson | 435/6 |

OTHER PUBLICATIONS

Wang et al, "Phase separations of alpha-tocopherol in aqueous dispersions of distearoylphosphatydylethanolamine", Chemistry and Physics of Lipids, 114, pp. 1-9 (2002).*
Tenchov et al, "Accelerated Formation of Cubic Phases in Phosphatidylethanolamine Dispersions", Biophysical Journal, vol. 75, Issue 2, pp. 573-1138 (Aug. 1998).*
International Search Report for PCT/GB2004/003387 dated Nov. 9, 2004.
Barauskas et al, "Cubic Phase Nanoparticles (Cubosome): Principles for Controlling Size, Structure, and Stability", Langmuir 2005, 21, 2569-2577.

* cited by examiner

METHOD FOR IMPROVING THE PROPERTIES OF AMPHIPHILE PARTICLES

This application is the U.S. national phase of international application PCT/GB2004/003387 filed 4 Aug. 2004, which designated the U.S. and claims benefit of GB 0318244.1 filed 4 Aug. 2003, GB 0322279.1 filed 23 Sep. 2003, GB 0401514.5 filed 23 Jan. 2004, and GB 0412671.0 filed 7 Jun. 2004, the entire contents of each of which are hereby incorporated by reference.

The present invention relates to methods for the production of particles suitable for the delivery of active substances. More specifically, the invention relates to methods for the production of non-lamellar amphiphile-based particles and for controlling the particle size distribution thereof.

BACKGROUND OF THE INVENTION

Amphiphile-based formulations show considerable potential in the delivery of many substances, especially for in vivo delivery to the human or animal body.

Because the amphiphile has both polar and apolar groups which cluster to form polar and apolar regions, it can effectively solubilise both polar and apolar compounds.

In addition, many of the structures formed by amphiphiles/structuring agents in polar and/or apolar solvents have a very considerable area of polar/apolar boundary at which other amphiphilic compounds can be adsorbed and stabilised.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ "sponge" phase which comprises a multiply interconnected three-dimensional bi-continuous network of bilayer sheets which lack the long-range order of the liquid crystalline phases. Depending upon their curvature, these phases may be described as normal (mean curvature towards the apolar region) or reversed (mean curvature towards the polar region). Where the spontaneous curvature of the lipid system is close to zero, the structures are typically lamellar, such as uni- or multi-lamellar vesicles/liposomes and where the spontaneous curvature is more negative or positive, cubic, hexagonal and micellar phases typically dominate.

The non-lamellar liquid crystalline and $L_3$ phases are thermodynamically stable systems. That is to say, they are not simply a meta-stable state that will separate and/or reform into layers, lamellar phases or the like, but are the thermodynamically stable form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area between polar and apolar regions. This has led to considerable investigation of non-lamellar phases particularly in controlled-release formulations and for solubilising compounds of relatively low solubility.

As discussed above, a bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk non-miscible phase would cause problems, such as in parenteral applications. Further control of a compound's transport properties and release profile may also be achieved by such a dispersion of non-lamellar particles.

Liquid crystalline or $L_3$ phase can be in or near thermodynamic equilibrium with the excess solvent and may be dispersed into colloidally stable dispersions of non-lamellar particles. Such particles may be fully (i.e. thermodynamically) stable, or may gradually degrade, thereby providing control over the release profile for active agents formulated therewith. The formation of dispersions can be spontaneous or as the result of mechanical force such as shearing or ultrasound. These non-lamellar particles are of considerable interest in the delivery of active agents and have been proposed as carriers for many such actives.

A method for the formation of dispersed particles of non-lamellar phase in solvents such as water is described in U.S. Pat. No. 5,531,925. Such particles have a non-lamellar liquid crystalline or $L_3$ interior phase and a lamellar or $L_3$ surface phase and may also contain active ingredients.

Known particles of liquid crystalline or $L_3$ interior phase may be formed by methods such as adding to this phase a solution of surface-phase forming agent, stirring to form a coarse dispersion and fragmenting the resulting mixture.

In order to assess the presence of a liquid crystalline phase, the prospective liquid crystalline material may be examined by use of small-angle X-ray diffraction (SAX), cryo-Transmission Electron Microscopy (cryo-TEM) or Nuclear Magnetic Resonance (NMR) spectroscopy studies. The sizes and size distributions of the dispersed particles may be examined by light scattering, particularly by use of laser light scattering instruments.

Dispersions containing active ingredients and particularly those for intravenous administration to the human or animal body are desirably colloidal, that is they should be of a particle size no greater than 10 µm, especially no greater than 5 µm and particularly no greater than 1 µMm. If particles within the dispersion exceed this size then the dispersion may not be colloidally stable and may settle or float from the dispersion. There is also a considerable risk of causing embolism when the preparation is administered intravenously. Furthermore, it is desirable that the distribution of particle sizes be narrow to maximise control over the release of any active agent. Where a particulate composition is to be administered by a method other than intravenously (e.g. orally, intramuscularly, subcutaneously, rectally or by inhalation), then the particles need not necessarily be colloidal but it remains advantageous to provide a well characterised and reproducible particle size distribution in order to control the rate of in vivo transport and decomposition of the particles and/or release of the active agents.

The particle size of a particulate composition should also be stable to storage over a considerable period of time. If the distribution of particle sizes changes significantly then the effective transport rate for composition (e.g. due to diffusion and rate of release of any active agent) may be adversely affected. Of still greater concern is the stability of particle sizes in a colloidal dispersion for intravenous administration. If the particle size distribution of such a dispersion is not stable (e.g. to storage and distribution) then large particles may form over time and be dangerous when administered. Even if not directly dangerous, storage instability can cause significant variability in pharmacokinetics, dynamics and/or efficacy.

In addition to control over particle size, it is desirable to maximise the proportion of particles which are in the desired, non-lamellar, phase in order to maximise the beneficial effects of this in terms of loading capacity, protective encapsulation, controlled release, reproducibility etc. The proportion of lamellar particles such as uni- or multi-lamellar vesicles should therefore be minimised.

Known methods for the formation of dispersed particles of non-lamellar phase are highly effective, but typically produce a relatively broad distribution of particle sizes and a considerable proportion of "contaminant" lamellar vesicular particles. Increasing the proportion of fragmenting and/or stabilising agent (e.g. surfactant, copolymer and/or protein) in the formulation or increasing the energy input of the homogenisation process may be used to narrow the particle size distribution but at the expense of increasing the proportion of lamellar particles. There is therefore a considerable need for methods by which a dispersion of non-lamellar particles may be formed having a narrow, preferably colloidal, particle size distribution and a high proportion of non-lamellar particles.

The present inventors have now unexpectedly established that by heating lamellar and/or non-lamellar particles of appropriate composition to an elevated temperature for a short period before cooling to room temperature, the distribution of particle sizes may be narrowed, the stability of the particle size distribution improved and/or the proportion of non-lamellar particles increased.

BRIEF DESCRIPTION OF THE INVENTION

In its first aspect, the present invention thus provides a method for forming a dispersion comprising non-lamellar amphiphile particles having improved phase behaviour, particle size distribution and/or storage stability, said method comprising forming a dispersion of lamellar and optionally non-lamellar particles comprising at least one structuring agent, heating said particles to an elevated temperature, followed by cooling, wherein said heating is to a temperature and for a period sufficient to provide, after cooling, a measurable improvement in phase behaviour, particle size distribution and/or storage stability. In this and all similar methods of the invention, the heat treatment is most conveniently carried out with the amphiphile particles in the form of a dispersion in a polar solvent.

One aspect of this improvement in particle properties is an "improvement" in phase properties, which herein indicates the provision of a greater proportion of non-lamellar phase particles.

In one aspect, the present invention therefore provides a method for the production of (preferably colloidal) non-lamellar particles, said method comprising forming lamellar and optionally non-lamellar particles comprising at least one structuring agent, heating said particles to an elevated temperature, followed by cooling, preferably to ambient temperature, wherein said heating is to a temperature and for a period sufficient to provide conversion of at least 50% of said lamellar particles to non-lamellar form, after cooling. This heating and cooling method may be carried out once, or as two, three, four or more sequential cycles of heating and cooling.

In a further aspect, the present invention further provides a method for narrowing the particle size distribution (for example, as displayed by light scattering) of a sample of lamellar and/or non-lamellar particles comprising at least one structuring agent, said method comprising heating said particles to an elevated temperature, followed by cooling, preferably to ambient temperature, wherein said heating is to a temperature and for a period sufficient to provide a narrowing of said particle size distribution after cooling. This heating and cooling method may be carried out once, or as two, three, four or more sequential cycles of heating and cooling.

Because lamellar and non-lamellar particles are self-assembled systems, particles of a dispersion may collide and fuse, thereby broadening the distribution of particle sizes when the dispersion is stored. Ostwald ripening may also contribute to broadening of the distribution during storage. It has, remarkably, been established that the method of heat cycling may render the distribution of particle sizes in a dispersion of lamellar and/or non-lamellar particles more stable over time.

In a further aspect, the present invention therefore provides a method for stabilising the particle size distribution (for example, as displayed by light scattering) of a sample of lamellar and/or non-lamellar particles comprising at least one structuring agent, said method comprising heating said particles to an elevated temperature, followed by cooling, preferably to ambient temperature, wherein said heating is to a temperature and for a period sufficient to provide stabilisation of said particle size distribution after cooling. This heating and cooling method may be carried out once, or as two, three, four or more sequential cycles of heating and cooling.

The heat cycling methods of the invention have surprisingly general application and appear suitable for the control of phase, particle size distribution and/or stability of many dispersed lipid formulations, especially where the thermodynamic state of the composition is non-lamellar at ambient temperature.

In a further aspect, the present invention provides non-lamellar particles comprising at least one structuring agent formed or formable by forming lamellar and optionally non-lamellar particles comprising at least one structuring agent, heating said particles to a temperature at which conversion to non-lamellar particles takes place for a period sufficient to provide conversion of at least 50% of said lamellar particles to non-lamellar form, followed by cooling, preferably to ambient temperature. The particles may be non-colloidal (e.g. 10-200 µm), for example where the formulation is to be suitable for non-intravenous use, but are preferably colloidal.

BRIEF DESCRIPTION OF THE DRAWINGS

The invention will be illustrated below by the following non-limiting examples and the accompanying figures in which.

DETAILED DESCRIPTION OF THE INVENTION

Figure 1:
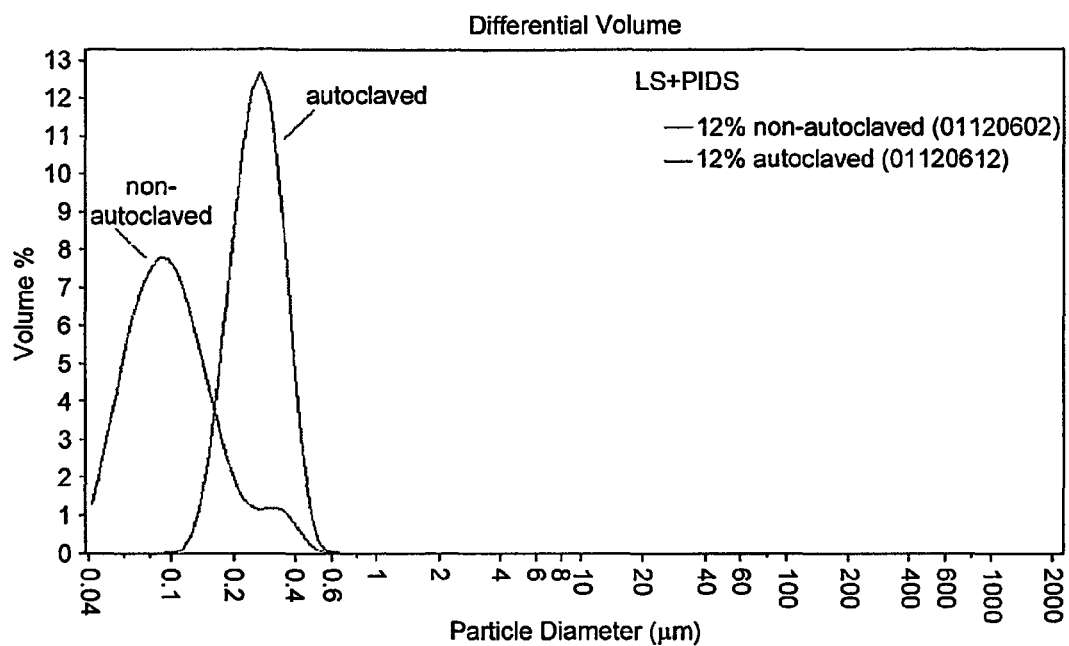
FIG. 1 shows the particle size distribution of a sample of GMO with 12% poloxamer before and after heat treatment.

In a further embodiment of the invention, the present inventors have additionally established that the particle size distribution of a formulation comprising at least one structuring agent for use in the present invention may be controlled further by carrying out the heat treatment of the present invention in an aqueous medium of controlled ionic strength. In particular, small (e.g. colloidal, especially small colloidal (<0.3 µm)) particles are most easily formed at low ionic strength such as below or around 0.1 mM NaCl in water. The proportion of non-lamellar particles (i.e. having a non-lamellar core as described herein) is increased by use of the heat cycling method described herein. The particle size distribution may be controlled by heat treatment in a medium (generally an aqueous solution) of controlled ionic strength. The average particle size is generally increased by use of media with higher ionic strength. Typically, stable, non-lamellar particle dispersions may be formed by carrying out the heat treatment step at ionic strength in the range 0.1 mM to 100 mM NaCl (or ionic strength equivalent) depending upon the composition used. The precise size distribution will depend upon the composition and suitable conditions may quickly be established by reference to the methods described herein, but typically sub-micron particles are formed at low ionic strength and larger colloidal and non-colloidal particles at increasing ionic strengths.

Where small particles are required in solutions of relatively high salt concentrations (e.g. in 0.9% NaCl for injections) the particles may be formed by the heat treatment method of the invention at a low ionic strength and, after cooling, further salt(s) added to provide the desired osmolality.

Furthermore, where a proportion of a charged amphiphile is included in the amphiphilic components of a composition, it is desirable to conduct heat treatment step at an ionic strength of around 0.1-20 mM NaCl, or an equivalent level of other suitable salt(s). The most desirable range will depend upon the particular components of the composition and will typically be 0.1 to 15 mM, preferably 0.2 to 10 mM. By doing so, the proportion of particles converted to non-lamellar form is increased while maintaining the particle size in a desirable size range.

In a yet further embodiment of the invention, the present inventors have further established that the particle size distribution of a formulation comprising at least one structuring agent for use in the present invention may be further controlled by carrying out the methods of the present invention in an aqueous medium at controlled concentration of amphiphile. In particular, small (e.g. colloidal, especially small colloidal (<0.3 µm)) particles are most easily formed at low concentration of amphiphile, such as below or around 10 wt % total amphiphile in aqueous solution. The proportion of non-lamellar particles (i.e. having a non-lamellar core as described herein) is increased by use of the heat cycling method described herein and/or the particle size distribution may be narrowed as also described.

The particle size distribution may be controlled by treatment at a known and controlled concentration (generally in aqueous solution). The average particle size generally being increased by use of higher total amphiphile concentrations. Typically, stable, non-lamellar particle dispersions may be formed by carrying out the methods of the invention (e.g. as described in any of the examples herein) at amphiphile concentrations of 0.5 to 20 wt %, preferably 1 to 15 wt % in an aqueous medium. The precise size distribution will depend upon the composition and suitable conditions may quickly be established by reference to the methods described herein. Typically, sub-micron particles are formed at high dilution and larger colloidal and non-colloidal particles at increasing amphiphile concentrations. The effect of dilution may be used in combination with any of the other factors considered herein (especially number of heat-cool cycles, cycle time, ionic strength etc.) to control the average size, size distribution and/or phase behaviour of an amphiphile system (as describe herein). By reference to the Examples below a skilled worker will have little difficulty establishing suitable conditions for a desired amphiphile mixture.

Where small particles are required at relatively high concentrations of amphiphile (e.g. to minimize the total volume for injections) the particles may be formed by the methods of the invention at high dilution and, after cooling, concentrated by evaporation, ultrafiltration etc. Conversely, where larger particles are required at high dilutions (e.g. for infusion to a subject) then these may be formed by the processes described herein at high concentrations and, once cooled, diluted further.

As used herein, the term "non-lamellar" is used to indicate a normal or reversed liquid crystal phase (such as a cubic or hexagonal phase) or the $L_3$ phase or any combination thereof, as opposed to lamellar structures as found in lamellar phase of liposomes. Where a particle is described as having a non-lamellar phase or form, this indicates that at least the internal region of the particle should adopt this form. The particles will generally have two distinct regions, an internal region and a surrounding surface region. The surface region, even in a "non-lamellar" particle will often be lamellar or crystalline and may be any phase ranging from a highly ordered crystalline or liquid crystal phase to a virtually orderless fluid layer. In contrast, a "lamellar" particle, as described herein is a particle having a solvent, rather than non-lamellar, core-region.

The term "lamellar particles" is used herein to indicate vesicular particles characterised in that they comprise one or more outer lamellar bilayers of amphiphile, surrounding an inner solvent compartment.

The temperature to which the particles must be heated in order to provide the effect of the present invention will be readily established by one of skill in the art. For example, a sample of lamellar particles may be heated to a particular temperature for 4 hours and subsequently cooled to ambient temperature. The SAX scattering pattern of the sample before and after heat treatment may then be compared and the results compared for the presence of peaks corresponding to, for example, reversed cubic or hexagonal phase. Similarly, the length of time required for conversion at any particular temperature may be assessed by heating samples for set times and examining any changes in SAX scattering. Equivalent heating experiments will also determine the effect upon particle size distribution and storage stability, using analytical tools such as light scattering and cryo transmission electron microscopy.

Typically, samples will be heated to a temperature in the range 75 to 200° C., preferably 85 to 150° C., more preferably 96 to 140° C. The most preferred temperature range is 100 to 130° C. The heat may be supplied by any appropriate method, such as by autoclaving, baking in an oven, by electromagnetic irradiation (e.g. infra-red or microwave irradiation) and/or alternatives known in the art.

It has been surprisingly established that the temperature cycling method of the present invention functions without the need for the equilibrium form of the composition to be non-lamellar at the elevated temperature. For example, a cubic phase may be the equilibrium condition for a composition at temperatures from ambient to 90° C. and the elevated temperature be 100° C. At this elevated temperature, the equilibrium condition for a composition may not be non-lamellar. For example, the equilibrium condition for the composition at the elevated temperature may be lamellar, micellar (e.g. L1, L2) or isotropic, especially $L_2$.

Alternatively, the equilibrium form of the composition at the elevated temperature may be a different non-lamellar phase to that produced upon cooling. Thus, the composition may be heated, for example to an elevated temperature at which a hexagonal liquid crystalline phase is the equilibrium form and then cooled to a temperature at which the particles re-form to give bicontinuous cubic phase particles.

Thus, the present invention also provides a method for the production of (preferably colloidal) non-lamellar particles, said method comprising forming lamellar and optionally non-lamellar particles comprising at least one structuring agent, heating said particles to an elevated temperature at which temperature the equilibrium form of the particles is not non-lamellar (e.g. is not liquid crystalline and is preferably lamellar, micellar (e.g. L1, L2), or isotropic), followed by cooling, preferably to ambient temperature, wherein said heating is to a temperature and for a period sufficient to provide conversion of at least 50% (by particle number) of said lamellar particles to non-lamellar (especially liquid crystalline) form, after cooling. This heating and cooling method may be carried out once, or as two, three, four or more sequential cycles of heating and cooling.

Typical periods of heating at an elevated temperature are relatively short and will generally be between 1 minute and 4 hours, more typically between 2 minutes and 1 hour. Periods of between 2 and 30 minutes are preferred, particularly between 5 and 20 minutes. The period may optionally include a period for temperature equilibration, typically 1-10 minutes.

The components of the formulations include at least one structuring agent (typically an amphiphile) and will generally also include a fragmentation agent (which may also be an amphiphile, such as a surfactant, copolymer and/or protein). In addition, the formulations of the invention may include protein, drug, nutrient, cosmetic, diagnostic, pharmaceutical, vitamin, or dietary agents at a level sufficient to be effective without disrupting the phase behaviour of the composition in such a way that a non-lamellar phase is no longer formed. These are referred to herein as "active agents". Under some circumstances the structuring agent or fragmentation agent may also be an active agent. It is preferable that the thermodynamic equilibrium state of the component mixture of the formulation at ambient temperature, optionally in the presence of a solvent (such as water) is a non-lamellar phase such as the normal or reversed cubic or hexagonal phases or $L_3$ phase.

Where an active agent is formulated in a composition of or for use in the method of the invention, the active agent will frequently have an effect upon the phase behaviour of the structuring agent(s). For example, certain active agents (such as cyclosporin A) introduce greater negative curvature than some structuring agents and at high concentrations may cause the formation of highly negatively curved phases, such as the reversed micellar $L_2$ phase rather than a cubic or hexagonal liquid crystalline phase. Nonetheless, such an active agent could be formulated into, for example, a reversed hexagonal phase by formulation with a structuring agent, or a blend thereof, having a less negative spontaneous curvature. By this method, the overall mixture provides the appropriate negative curvature to allow use in the methods or compositions of the invention.

The skilled worker will be able to use standard methods to assess the degree of spontaneous curvature of any particular structuring agent (or mixture thereof) or the effect on this by including an active agent. This might be done, for example, by studies of the bulk phase behaviour of each structuring agent in water and subsequent studies with varying concentrations of active agent included. The phases can be examined by any of the methods indicated herein (e.g. polarised light, SAXS cryo-TEM etc.) and an appropriate blend of structuring agents chosen for each case. In some circumstances, where the effect of the active agent on the phase behaviour of the mixture is significant, the structuring agent(s) chosen may not provide the desired non-lamellar phase in themselves (e.g. may have too small or too great spontaneous curvature) but will generate this phase only when also formulated with the active agent. Similarly, the equilibrium phase may change from, for example, cubic to hexagonal liquid crystalline phase upon addition of the active agent.

The polar solvent referred to herein will generally be an aqueous solvent such a purified water, saline, buffer, solutions of salts, sugars and/or water soluble polymers and the like. Such solvents may also contain a proportion of water soluble organic solvents such as alcohols (e.g. ethanol or iso-propyl alcohol), esters (e.g ethyl acetate) and the like.

The term structuring agents, as used herein in the methods and compositions of the invention, are any agents that are capable of forming a non-lamellar phase, optionally in the presence of other agents such as amphiphiles and/or fragmentation agents. Structuring agents will generally have at least one polar, hydrophilic group and at least one non-polar, hydrophobic group. A wide range of structuring agents are applicable for use as all or part of the structuring agent component.

Examples of polar groups are well known (see e.g. US published patent application number 20020153509) and include anionic groups such as carboxylates, phosphonates, sulphates and sulphonates, non-ionic groups such as alcohols, polyols (eg sugars, glycerol etc) and esters, cationic groups such as quaternary ammonium compounds, pyridinium salts and quaternary phosphonium salts and zwitterionic groups such as phospholipid head groups (e.g phosphatidyl-choline, phosphatidic acid, phosphocholine, phosphoethanolamine, phosphoglycerol, phosphoserine, their PEGylated or mPEGylated derivatives, etc.), ammonioacetates, ammonio-alkanesulphonates and trialkylaminoalkylphosphate esters.

Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Y indicates a hydrocarbon chain having X carbon atoms and Y unsaturations. Examples particularly include caproyl (C6:0), caproyl (C8:0), capryl (C10:0), lauroyl (C12:0), myristoyl (C14:0), palmitoyl (C16:0), phytanoyl (C16:0), palmitoleyl (C16:1), stearoyl (C18:0), oleoyl (C18:1), elaidoyl (C18:1), linolenoyl (C18:2), linolenoyl (C18:3), arachidonoyl (C20:4), behenoyl (C22:0) and lignoceroyl (C24:9) groups. An amphiphile will typically have one or two non-polar "tail" groups (mono-acyl and di-acyl lipids respectively) but may have three, four or more hydrophobic groups.

Examples of structuring agents suitable for use in the present invention include natural lipids, synthetic lipids, surfactants, copolymers, peptides, proteins, hydrotropes, alcohols, and other additives that may form or facilitate formation of non-lamellar structures. Preferred agents are glycerides (e.g. monoglycerides, diglycerides, and triglycerides), di- and polyglycerolesters of glycerides (e.g. digylcerol monooleate, digylcerol monocaprate), natural fats and oils (e.g. soybean oil, coconut oil, corn oil, castor oil, sunflower oil), fractionated oils (e.g. fractionated coconut oil, Miglyol® (Condea)), transesterified oils (e.g. Maizine®), transesterification products of oils and PEG (e.g. ethoxylated castor oil (e.g. Cremophor® EL (BASF)), ethoxylated hydrogenated castor oil (e.g. Cremophor® RH-40 (BASF)), ethoxylated corn oil (e.g. Labrafil® M 2125 CS (Gattefossé))), acetylated monoglycerides, fatty acids (e.g. $C_6$-$C_{26}$ saturated and unsaturated fatty acids), fatty alcohols (e.g. phytantriol (3,7,11,15-tetramethyl-1,2,3-hexadecantriol)), ether lipids (e.g. monooleoyl glyceryl ether), natural and synthetic phospholipids (e.g. egg lecithin, soya lecithin, hydrogenated lecithin, phosphatidyl choline, phosphatidyl ethanolamine, phosphatidyl serine, phosphatidyl glycerol, phosphatidic acid), lysophospholipids (e.g. lyso-lecithin, lyso-phosphatidyl choline, lyso-oleyl phosphatidyl choline), phospholipid-analogous compounds (e.g. those disclosed in U.S. Pat. No. 6,344,576), sterols and sterol derivatives (e.g. cholesterol, sitosterol, lanosterol and their esters, especially with PEG or fatty acids), galactolipids (e.g. digalactosyl diacylglycerol, monogalactosyl diacylglycerol), sphingolipids (e.g. sphingomyelin); nonionic surfactants, in particular ethoxylated surfactants such as PEG-fatty acid mono- and diesters (e.g. of the Crodet® (Croda), Cithrol® (Croda), Nikkol® (Nikko), Myrj® (ICI) series, Solutol® HS 15 (BASF)), PEG glycerol fatty acid esters (e.g. Tagat® L and O (Goldschmidt), Glycerox® L series (Croda), Capmul® EMG (Abitec)), transesterification products of oils and PEG (e.g. of the Labrafil® (Gattefossé), Cremophor® (BASF) Crovol® (Croda) and Nikkol® HCO (Nikko) series), PEG-sorbitan fatty acid esters (e.g. Tween® 20, Tween® 80 and other polysorbates of the Tween® series (ICI)), PEG alkyl esters (e.g. of the Brij® (ICI) and Volpo® (Croda) series), PEG alkyl phenol surfactants (e.g. of the Triton X and N series (Rohm & Haas); polyglycerised fatty acids (e.g. Nikkol® Decaglyn (Nikko), Plurol® Oleique (Gattefossé)), propylene glycol fatty acid esters), propylene glycol fatty acid esters (e.g. Capryol® 90 (Gattefossé), Lutrol® OP2000 (BASF), Captex® (Abitec)), glycerol/propylene glycol fatty acid esters (e.g. Arlacel® 186 (ICI)), sorbitan fatty acid esters (e.g. of the Span® (ICI) and Crill® (Croda) series), sugar esters (e.g. of the SUCRO ESTER® (Gattefossé), Ryoto® (Mitsubishi-Kagaku) and Crodesta® (Croda) series), polyoxyethylene-polyoxypropylene block copolymers (so-called poloxamers, e.g. of the Pluronic® (BASF), Synperonic® (ICI) and Lutrol® (BASF) series), copolymers of ethylene oxide and butylene oxide; anionic surfactants including fatty acid salts, bile salts (e.g. sodium cholate, sodium glycocholate, sodium taurocholate), carboxylates such as ether carboxylates, succinylated monoglycerides, mono/diacetylated tartaric acid esters of mono- and diglycerides, citric acid esters of mono- and diglycerides, glyceryl-lacto esters of fatty acids, acyl lactylates, alginate salts, propylene glycol alginate; cationic surfactants including ethoxylated amines (e.g. polyoxyethylene-15 coconut amine), betaines (e.g. N-lauryl-N,N-dimethylglycine), alkylpyridinium salts, quaternary ammonium salts such as hexadecyl triammonium bromide, decyl trimethyl ammonium bromide, cetyl trimethyl ammonium bromide; zwitterionic surfactants including trimethylammonioethyl-alkylphosphonates (e.g. the examples disclosed in U.S. Pat. No. 6,344,576); and all mixtures thereof. The most preferred structuring agents are glycerol monooleate (GMO) glycerol monolinoleate digylcerol monooleate (DGMO) digylcerol monolinoleate, glyceryl dioleate, dioleyl phosphatidyl ethanolamine (DOPE), dioleyl phosphatidylcholine (DOPC) and phytantriol, and mixtures of these with up to 50% fatty acids, in particular oleic acid and linoleic acid, polysorbate 80 (Tween® 80), polyethylene glycol 660 12-hydroxysterate (Solutol® HS 15), or lyso-phospholipids, especially lyso-oleyl phosphatidylcholine (LOPC).

Often the structure forming agent component will contain components in the form of extracted and purified natural products and will thus contain a mixture of related compounds. Soy bean phosphatidyl choline, for example is a mixture of compounds having around 60-75% C18:2 acyl groups, around 12-16% C16:0 and the balance others.

Similarly, commercial glycerol monooleate is typically at least 90% monoglyceride but contains small amounts of diglyceride and free fatty acid, with the acyl groups being over 60-90% C18:1, 5-10% saturated and the remainder largely higher unsaturated acyl groups. Different commercial preparations will also vary slightly as indicated in the Examples below.

A highly preferred structuring agent for use in the present invention is commercially available glycerol monooleate (GMO). As indicated above, this is largely monoglyceride with an oleoyl (C18:1) acyl chain but contains certain amounts of other compounds. These are included in the term "glycerol monooleate" or "GMO" as used herein. Commercial preparations of GMO include GMOrphic-80 and Myverol 18-99 (available from Eastman Kodak), Rylo MG 19 and Dimodan distilled-GMO (available from Danisco). Any of the structuring agents may be used alone or in combination with one or more other structuring agents.

In addition to the amphiphilic structuring agent component, the compositions of the invention may, in particular, include at least one fatty acid or fatty acid salt component. Preferred fatty acids have between 6 and 24 carbons and particularly those corresponding to the fatty acid chains of natural lipids, including caproic, caprylic, capric, lauric, myristic, palmitic, phytanic, palmitoleic, stearic, oleic, elaidic, linoleic, linolenic, arachidonic, behenic or lignoceric acids, their salts or mixtures thereof. The fatty acids may be saturated but are preferably unsaturated. The most preferred fatty acid is oleic acid. Salts of fatty acids will typically be physiologically tolerable, and for pharmaceutical applications will always be so. Preferred salts include alkali and alkaline earth metal salts such as sodium, potassium, lithium, calcium or magnesium salts as well as ammonium and alkylammonium salts. Typically, the fatty acid or fatty acid salt will be present as 0-10 wt % of the total amphiphilic component, preferably 3-7% by weight.

The fragmentation agent for use in the method of the invention will be at least one agent which aids the dispersal of the non-lamellar phase into particles or stabilises such particles. Typically a fragmentation agent will be a surfactant such as an amphiphilic block copolymer. A large number of surfactants and copolymers are suitable for use as all or part of the fragmentation agent for use in the present invention.

Important fragmentation agents include natural lipids, synthetic lipids, surfactants, copolymers, proteins (in particular caseins and albumin), hydrotropes, alcohols and other additives that may facilitate fragmentation spontaneously or with the aid of externally applied forces and pressures and contribute to stabilisation. This includes also nanoparticles and combinations of polymer and nanoparticles (see e.g. WO 99/12640).

Suitable copolymers for use as fragmentation agents may have blocks comprising polyoxyalkylenes, polyvinylpyrrolidone, polyvinylacetate, polyvinylalcohol, polyesters, polyamides and/or polyalkenes. The block copolymer will comprise at least two blocks of polymer having different degrees of hydrophilicity. Certain proteins (such as casein) are also of amphiphilic character and may be used as fragmentation agents. Where an active agent is an amphiphilic protein, this may act as both the active agent and the fragmentation agent, or may be included in addition to another active agent and/or fragmentation agent.

Preferred examples of amphiphilic block copolymers are poloxamers, which comprise at least one block of polyoxyethylene and at least one block of polyoxypropylene. The most preferred fragmentation agents are poloxamer 407 (e.g. Pluronic® F127, BASF), poloxamer 188 (e.g. Pluronic® F68, BASF), poloxamer 124 (Pluronic® L44, BASF), and polysorbates 20, 60 and/or 80 (referred to herein a P20, P60 & P80 respectively—e.g. Tween® 80, ICI). Other suitable surfactants and copolymers may be found in the "Handbook of Pharmaceutical Excipients" (2nd Ed., the American Pharmaceutical Association and The Pharmaceutical Press, Royal Pharmaceutical Society of Great Britain).

Other preferred fragmentation agents include polyethylene glycol lipid conjugates (e.g. PEGylated and mPEGylated phospholipids) as well as long chain alcohols and fatty acids.

In a preferred embodiment of the present invention, the compositions used, formed and/or formable in the method of the invention have a ternary amphiphilic composition comprising at least one structure forming amphiphile (component a), at least one "structure swelling" agent (component b) and at least one dispersion stabilising "polymeric" agent (component c). Components b and c will also act as fragmentation agents. In this embodiment, at least 50% by weight of the total amphiphilic components (a+b+c) should be component a.

Preferably this will be 60 to 95%, more preferably 70 to 90%. Correspondingly, component b should be less than 40% by weight of a+b+c, preferably 5 to 30% and more preferably 10 to 25%. Component c should be present at less than 20%, preferably 1 to 15% and more preferably 2 to 10% of the total weight of a+b+c.

Compositions comprising components a, b and c as described herein are highly suitable for use in the methods of the present invention in that they typically have a thermodynamically stable non-lamellar state in an appropriate aqueous medium. Furthermore, the compositions may have favourable in vivo properties such as low hemolytic effects and low acute toxicity, thereby providing enhanced utility as carriers for active agents such as drugs and/or nutrients (see active agents indicated herein).

In the ternary amphiphilic compositions, structure forming component "a" will preferably comprise at least one lipid component such as glycolipids, diglycerides and/or phospholipids (e.g phosphatidyl ethanolamines). Naturally occurring lipids are particularly suitable but non-naturally occurring variants such as ether lipids (having a head and tail group joined by an ether bond) are also suitable. Lipids such as diacyl phosphatidyl ethanolamines, and diacylglycerols and diacyl phosphatidyl cholines are highly suitable.

In this embodiment, component a may also contain up to 10% (e.g. 1-10% by weight of this component) of at least one charged amphiphile, particularly anionic lipids (such as acyl or diacyl phosphatidyl glycerols) or fatty acid (see above). Correspondingly, 90% or more, preferably at least 95% of the component a should preferably have no net charge under neutral and/or physiological conditions. Component a when formulated alone in excess water should form a reversed non-lamellar phase, preferably a reversed hexagonal phase.

The structure swelling component "b" is generally a component which swells the lattice of the amphiphilic structure allowing it to more readily be dispersed into particulate form. This component may also facilitate structural transition, for example, from reversed cubic to hexagonal phase structures. Structure swelling agents will generally have a relatively low molecular weight (e.g. less than 2000) and are preferably components such as oligoethylene oxide based surfactants. Preferred examples of oligoethylene oxide based surfactants are those having between 5 and 40 ethylene oxide units bonded to a non-polar "tail" group (e.g. as an ester to a fatty acid, such as any of those described herein, or as an ether to a corresponding fatty alcohol). Preferred examples include polyoxyethylene alkylethers, polyoxyethylene sorbitan fatty acid esters (polysorbates), polyoxyethylene stearates, polyoxyethylene castor oil derivatives and polyoxyethylene lipid derivatives. Most preferred examples are TMGO-15 (Nikko), Solutol HS15 (BASF) and polysorbate 80.

The polymeric component "c" is, in general, a component which improves the stability of the dispersion, particularly as colloidal particles. Polymeric components generally have a relatively high molecular weight (e.g. greater than 2000) and will have at least one polymeric or copolymeric portion in their molecular structure. Preferred polymeric components include polyethylene oxide copolymers and lipids derivatised with polyethylene oxide, hydrophobically modified polysaccharides and amphiphilic proteins. Poloxamers as described herein are particularly suitable as the polymeric components as are PEG-substituted lipids such as PEG-glyceroldioleate, PEG-dioleoyl phosphatidyl ethanolamine (in particular DOPE-PEG2000 and DOPE PEG-5000) or PEG-dioleoyl phosphatidyl serine. Suitable polymeric agents also include PEG-sorbitol tetraoleate (Nikko), cholesterol pullulan (NOF) and 2-Methacryloyloxyethyl phosphorylcholine n-butyl methacrylate co-block polymers (PUREBRIGHT MB-37-50T and PUREBRIGHT MB-37-100T from NOF). All amphiphiles suitable for use as polymeric component "c" also form preferred polymeric fragmentation agents.

Preferred examples of polyethylene oxide copolymers are poloxamers, which comprise at least one block of polyoxyethylene and at least one block of polyoxypropylene. The most preferred of these agents are poloxamer 407 (e.g. Pluronic® F127, BASF), poloxamer 188 (e.g. Pluronic® F68, BASF), poloxamer 124 (Pluronic® L44, BASF).

The fragmentation agent(s) will be present at a level sufficient to bring about the fragmentation of the structuring agent and/or to stabilise the fragmented non-lamellar phase particles. Such fragmentation may be spontaneous or may require physical fragmentation such as by shearing and/or ultrasonication. It is preferable that sufficient fragmentation agent is present that the non-lamellar particles are physically stable.

Preferred combinations of structure forming agents and fragmentation agents include combinations of GMO, GDO and/or DOPE with at least one of Poloxamer 407, Poloxamer 188, TMGO-15/DOPE-PEG(5000) and/or P80.

In one preferred embodiment, the compositions of and for use in the present invention consist of GMO and one or more fragmentation agents (such as poloxamers), with any optional active agent and/or aqueous component. In an alternative embodiment, since the invention is applicable to a wide range of compositions, the compositions may comprise other structuring agent(s) and/or fragmentation agent(s) (e.g. other lipids, surfactants and/or fatty acids), with GMO and/or poloxamer optionally also present, along with any optional components such as active agents, aqueous components etc.

Active agents suitable for inclusion in the methods and formulations of the present invention include human and veterinary drugs and vaccines, diagnostic agents, "alternative" active agents such as plant essential oils, extracts or aromas, cosmetic agents, nutrients, dietary supplements etc. Examples of suitable drugs include antibacterial agents such β-lactams or macrocyclic peptide antibiotics, anti fungal agents such as polyene macrolides (e.g amphotericin B) or azole antifungals, anticancer and/or anti viral drugs such as nucleoside analogues, paclitaxel, and derivatives thereof, anti inflammatories, such as non-steroidal anti inflammatory drugs, cardiovascular drugs including cholesterol lowering and blood-pressure lowing agents, analgesics, antidepressants including serotonin uptake inhibitors, vaccines and bone modulators. Diagnostic agents include radionuclide labelled compounds and contrast agents including X-ray, ultrasound and MRI contrast enhancing agents. Nutrients include vitamins, coenzymes, dietary supplements etc. The active agents for use in the present invention will generally not be poloxamers or acylglycerols.

Preferred active agents include human and veterinary drugs selected from the group consisting of peptides such as adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, peptide T and its related peptides calcitonins and their related peptides, cell surface receptor protein fragments, chemotactic peptides, cyclosporins, cytokines, Dynorphins and their related peptides, endorphins and P-lipotropin fragments, enkephalin and their related proteins, enzyme inhibitors, fibronectin fragments and their related peptides, gastrointestinal peptides, growth hormone releasing peptides, immunostimulating peptides, insulins and insulin-like growth factors, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides (e.g. ocreotide), substance P and its related peptides, transforming growth factors (TGF) and their related peptides, tumour necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenin, bone morphogenic proteins, chemokines, colony stimulating factors (CSF), cytokines, growth factors, interferons, interleukins, leptins, leukemia inhibitory factors, stem cell factors, transforming growth factors and tumor necrosis factors; selected from the group consisting of antivirals, steroidal antiinflammatory drugs (SAID), non-steroidal anti-inflammatory drugs (NSAID), antibiotic, antifungals, antivirals, vitamins, hormones, retinoic acid, prostaglandins, prostacyclins, anticancer drugs, antimetabolic drugs, miotics, cholinergics, adrenergic antagonists, anticonvulsants, antianxiety agents, tranquilizers, antidepressants, anesthetics, analgesics, anabolic steroids, estrogens, progesterones, glycosaminoglycans, polynucleotides, immunosuppressants and immunostimulants, cardiovascular drugs including lipid lowering agents and blood-pressure lowering agents, bone modulators; vaccines, vaccine adjuvants, immunoglobulins and antisera; diagnostic agents; cosmetic agents, sunscreens and self-tanning agents; nutrients; dietary supplements; herbicides, pesticides, and repellents. Further examples of active agents can be found for instance in Martindale, The Extra Pharmacopoeia.

In the methods of the invention, particles comprising a structuring agent are formed prior to one or more heat treatment cycles. This pre-formulation will typically be in the form of a dispersion and may be prepared by established methods, such as those indicated in the present Examples and in U.S. Pat. No. 5,531,925, WO 02/02716, WO 02/068561, WO 02/066014 and WO 02/068562. The disclosures of these and all references cited herein are hereby incorporated herein by reference. Such methods include adding an amphiphile/water liquid crystal phase to an aqueous solution of fragmentation agent and optionally a lipid (such as PC) and either allowing natural fragmentation of the mixture or accelerating the process with, for example, mechanical agitation, vortexing, roto-stator mixing, high-pressure homogenization, microfluidisation and/or ultrasound.

Since the method of the present invention can be used to convert lamellar particles to non-lamellar form, it is not essential that the pre-preparation particles be non-lamellar. Thus, any of the well-known methods for formulating lipids into vesicles may be used to create pre-formulations for use in heat treatment methods of the present invention. Suitable methods include, for example, sonication or extrusion (such as through a polycarbonate membrane). Such methods will be well known to those of skill in the appropriate art.

The pre-formulations should, preferably, be formulated such that the thermodynamically stable state at ambient temperature is non-lamellar. Alternatively, the non-lamellar form may be a thermodynamically meta-stable state. Where present, the active agent may be incorporated into the particles prior to and/or after heat cycling. Where more than one heat cycle is used, the active agent may be incorporated between cycles.

Where the active agent is heat sensitive (e.g. peptide or protein) the active agent is preferably incorporated after heat cycling is complete.

The present inventors have further surprisingly established that the loading of active agent into amphiphilic compositions may be enhanced by one or more cycles of heat treatment as describe herein. A method of loading an active agent by heat cycling thus forms a further aspect of the invention, as do the products formed thereby.

In this aspect of the invention, the active agent must be stable to the conditions of the heat cycling. The active agents should thus be chemically stable in aqueous environments under the conditions of heat and duration described herein. The suitability of any active agent for this aspect of the invention may be established by routine testing under the heat-cycling conditions described herein. Preferred active agents in this respect include steroids such as progesterone, adrenocortical hormones, gonadal hormones, cardiac aglycones, bile acids abd sterols. Progesterone is particularly preferred.

Upon heat treatment by the method of the present invention in the presence of heat-tolerant active agents it has been noted that a loading level of several times that achieved by loading at room temperature can be generated. That is, at least twice the quantity of active agent can be incorporated into amphiphilic compositions described herein by heat treatment than can be incorporated by equilibration at room temperature. This ratio can be 3, 4 or 5 times and may be up to 6 or more with certain active agents. Furthermore, whether or not the active agent solubilised by this method is in a meta-stable state or in a truly stable dispersion or solution, the compositions loaded with up to 6 times the room temperature equilibrium level with active agent (especially steroid) have been observed to be stable to storage for at least two weeks. This offers considerable and obvious advantages in being able to provide high drug loads at while administering a small volume and low level of carrier to the subject.

Prior to, and/or after heat-cycling, the particles may be concentrated (e.g. by ultrafiltration or dialysis) and/or dried, for example by spray drying, fluid bed drying or freeze drying. In the case of dried particles, the drying process may be followed by particle size enlargement through single or repeated agglomeration and granulation steps. The concentrated, dried and/or agglomerated particle formulations thus formed may be used as such or hydrated and/or dispersed to yield non-lamellar particle dispersions suitable for use in the delivery of active substances, especially in vivo. Such concentrated, dried and/or agglomerated particle formulations and the dispersions resulting from their re-suspension/hydration form a further aspect of the present invention. Such drying need to be to remove all solvent from the amphiphile particles but should provide a solid, preferably a powder which is sufficiently "dry" to allow handling. Such powders are convenient intermediate formulations by which the particles may be formulated into gels and creams and the like.

In a preferred aspect of the invention, an initial pre-formulation, prior to heat treatment, is formed in which the particles will preferably be small colloidal sized particles, for example in the range 0.02 to 0.2 µm. Preferably the mean particle size for the small colloidal particles will be 0.05 to 0.15 µm in this pre-formulation. This small particle size can be achieved by known methods, as discussed above, but such methods result in a relatively large proportion of lamellar phase particles. At least one heat treatment cycle may then be applied to the pre-formulation so as to both convert the bulk of the lamellar particles to non-lamellar form and preferably also to narrow the particle size distribution. In this process, the mean particle size typically increases but the distribution of particle sizes is reduced. In this method, at least 50% (by particle number) of the lamellar particles should be converted to non-lamellar form. Preferably, at least 75% of the lamellar particles will be converted, more preferably at least 85% (e.g. 90%). It is most preferable that the treatment method convert 99% or more of the lamellar particles to a non-lamellar form.

Figure 3:
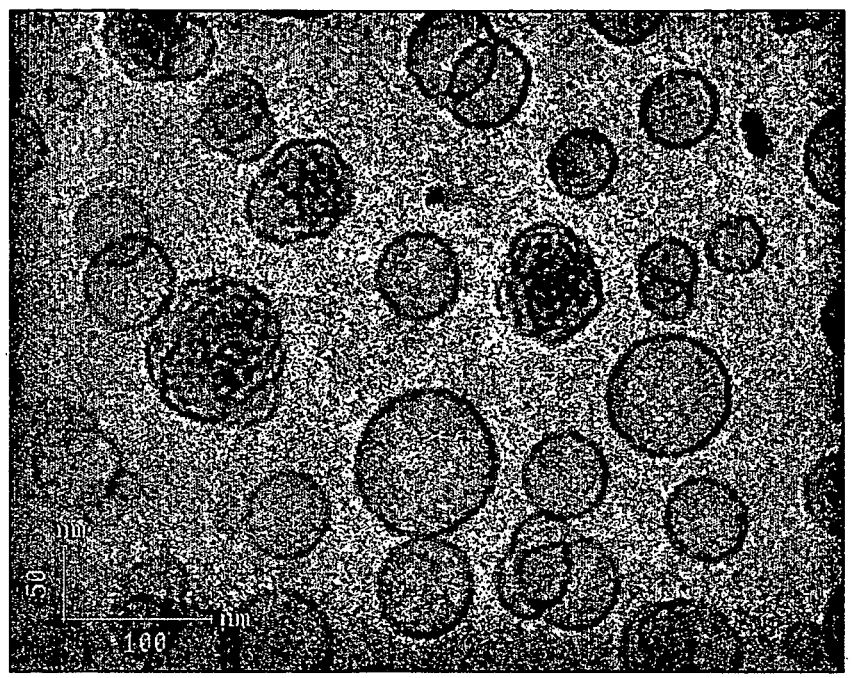
FIG. 3 shows a cryo-transmission electron micrograph of a sample without heat treatment.
Figure 4:
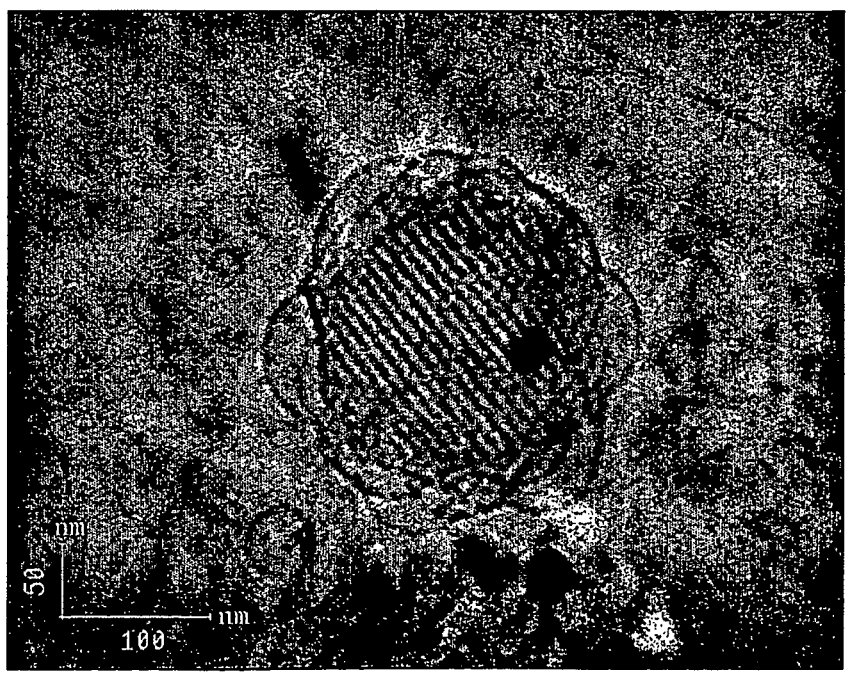
FIG. 4 shows a cryo-transmission electron micrograph of a sample after heat treatment.

The presence of particles in non-lamellar form will preferably be assessed from a set of cryo-transmission electron microscopy particle images. Such images will typically show at least 30 particles, preferably they will show a sample of more than 50 and most preferably more than 100 particles. Example images are shown in FIGS. 3 and 4. The presence of non-lamellar particles may also be assessed by X-ray scattering experiments.

After treatment with one or more heating and cooling cycles, the final particles should be in the colloidal size range. These will typically have an average (mode or preferably mean) particle size in the range 0.05 to 1 µm, preferably 0.1 to 0.8 µm (e.g. 0.2 to 0.8 µm), more preferably 0.2 to 0.6 µm (e.g. 0.3 to 0.6 µm). It is particularly important that preparations for use in intravenous administration should not contain particles in the non-colloidal range (e.g >1 µm or particularly >5 µm, and especially >10 µm, as indicated herein). For intravenous applications a preferred particle size range is 0.05 to 0.3 µm. This may be achieved by using the method of the invention, beginning with small colloidal particles as described above. Alternatively, or in addition, the particles, preferably after heat cycling, may be filtered in order to remove larger (e.g. non-colloidal) particles.

The samples of particles formed by the present invention have a greater proportion of non-lamellar particles, a narrower distribution of (especially colloidal) particle sizes and/or greater particle size stability than has been achieved by previous methods. Such particles therefore form a further aspect of the invention, as do dispersions thereof. The particles formed or formable by the method of the invention may be used in the production of nutritional, dietary, cosmetic, diagnostic veterinary or pharmaceutical compositions by known methods using well known carriers, excipients and other ingredients. In the case of pharmaceutical compositions, the particles will be formulated with at least one pharmaceutically acceptable carrier or excipient and may be formed into tablets, capsules and so forth. The particles may also be formulated as a pre-prepared dispersion in an acceptable liquid, such as water, or dried (e.g. spray dried or freeze dried) and sealed in sterile containers for re-suspension prior to administration.

In the formulations formed or formable by the method of the present invention, at least 75% (by volume) of the particles will preferably be non-lamellar. More preferably, at least 85% and most preferably at least 95% of particles in the formulation will be non-lamellar, as measured by volume. This measurement may be made by, for example, laser diffraction, preferably combined with cryo-TEM or SAXS (to confirm the non-lamellar particle structure).

In a further aspect, the present invention thus provides a formulation of (preferably colloidal) particles comprising at least one structuring agent, wherein at least 75% of the particles, preferably at least 85% and most preferably at least 95% of particles (as measured by volume) in the formulation are non-lamellar (e.g. as judged by laser diffraction combined with cryo-TEM or SAXS). In colloidal formulations, the average (mode or preferably mean) particle size will typically be in the range 0.1 to 1 µm (e.g. 0.3 to 0.6 µm), for example as determined by light scattering methods (e.g. laser diffraction). Preferably, no more than 1% of particles will be outside the range 0.05 to 1.5 µm, more preferably, not more than 0.1% will be outside this range, and most preferably no detectable (by laser diffraction) proportion of particles will be outside this range. In non-colloidal formulations the average particle size will typically be in the range 10 to 200 μm.

Furthermore, the colloidal formulations prepared by the method of the present invention are physically stable to storage over extended periods at ambient temperature. Such formulations should be essentially stable both in terms of phase behaviour and particle size for periods of at least 10 days at room temperature, more typically at least 3 months, preferably at least 6 months and more preferably 12 months or more. In contrast, even dispersions of similar average particle size which have not undergone treatment in the method of the invention may have particle sizes stable for less than 10 days at room temperature.

A particle size distribution can be considered essentially stable to storage if the average (mode or preferably mean) particle size increases no more than two fold during the storage period. Preferably, the average size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period. In a highly preferred embodiment, particle size distribution of the compositions formed or formable by the methods of the invention alter in average particle size and particle size distribution width at half-height by no more than 10% and remain monomodal on storage for the periods indicated above.

It is particularly important in the case of colloidal dispersions for use in intravenous or intra-arterial administration that the particle size distribution be stable to storage. A composition containing even a relatively small component of non-colloidal particles may cause embolism, or at least unpredictable rates of release upon administration directly to the blood stream. Similarly, the controlled release of an active agent may be dependent upon a reliable particle size distribution in a composition for administration by any other route. Pharmaceutical, diagnostic and veterinary products are also desirably stable to storage for several months or the cost and availability of the product is significantly adversely affected. The method of the invention thus significantly improves the prospect of an active agent formulated in a dispersion of non-lamellar particles forming a safe and available product.

It is additionally important that the phase structure of the particles in dispersion remains stable to storage so that the rate of release of any active agent may be effectively predicted. In a preferred embodiment, the particles of and formed by the method of the invention remain non-lamellar upon storage for the periods discussed above. By "remains non-lamellar" is indicated that no more than 10% of the non-lamellar particles should adopt a lamellar or micellar phase structure upon storage, preferably no more than 5% and more preferably no more than 2%.

It has additionally, most surprisingly been observed that the dispersions generated by the heat treatment method of the present invention are stable in dispersion at significantly higher concentrations of amphiphile than is typically the case. In particular, stability of non-lamellar (preferably colloidal) particles in dispersion has not previously been observed at above 1% total amphiphile in aqueous solvent. In contrast, the amphiphile particles of the present invention are observed to be stable to storage (as indicated above) at concentrations of at least 2%, preferably at least 4% and more preferably up to at least 6% by weight of total amphiphile. Stability may also be exhibited at concentrations up to at least 10% by weight amphiphile in water.

EXAMPLES

The materials used in the following examples were as follows:
GMOrphic-80 (Eastman Kodak)
Myverol 18-99 (Eastman Kodak),
Rylo MG 19 (Danisco)
Dimodan distilled-GMO (Danisco)
poloxamer 407 (Pluronic® F127, BASF)
poloxamer 188 (Pluronic® F68, BASF)
polysorbate 80 (Tween® 80, ICI)
Dioleoylphosphatidylethanolamine (DOPE)
  (from Avanti Polar Lipids or Lipoid)
Dioleoylphosphatidylglycerol (DOPG)
  (from Avanti Polar Lipids)
Glycerolmonooleate-PEG(660) (TMGO-15)
  (from Nikko Chemicals)
Dioleoylphosphatidylethanolamine-PEG(5000)
  (DOPE-PEG(5000))
  (from Avanti Polar Lipids)
Oleic acid (OA) (from Apoteket)

Approximate compositions of the batches used are shown below in Table 1

TABLE 1

| | Composition % | | | | |
|---|---|---|---|---|---|
| Trade Name | Mono-glyceride | Di-glyc-eride | C18:1 | Satu-rated | Higher unsatu-rated |
| GMOrphic-80 Lot No. D0116-1293 Batch No. 1997014177 | ≥94.0 | ? | ≥75 | ≤10.0 | ≤15.0 |
| Myverol 18-99 Batch No. 1996013291 | ≥90 | ? | 60–65 | 5–7 | ca. 30 |
| Dimodan distilled-GMO, NF Lot No. 70201 | 98 | 1.5 | 80 | 7.1 | 11.4 |
| Rylo MG 19, NF Lot No. 2119/53 | 98.7 | 1.0 | 90.3 | 4.7 | 6.6 |

In the following examples the abbreviations used are:
GMO Glycerolmonooleate
LD Laser Diffraction particle size measurement
LM Light microscopy
LS Light Scattering particle size measurement
P407 poloxamer 407
P188 poloxamer 188
PCS Photon Correlation Spectroscopy
PIDS Polarisation Intensity Differential Scattering
PSD Particle Size Distribution
SAXS Small Angle X-ray Scattering
TEM Transmission Electron Microscopy Example 1

Forming a Pre-Formulation

A coarse dispersion of largely cubic particles was formed by melting GMOrphic-80 (1.84 g) with poloxamer 407 (0.16 g) and adding 1.25 g of the molten mixture dropwise to deionised water (23.75 g) (containing 0.01% thiomersal as preservative) under stirring at room temperature. The resulting coarse dispersion was allowed to equilibrate for at least about 1 day before homogenisation in a microfluidizer at high pressure (350 bar) for 15 min at 40° C.

All of the dispersions used in the following Examples were prepared according to this standard procedure (Microfluidizer, 40° C., 350 bar, 15 min) with variations in composition (poloxamer/monoolein ratio and content and poloxamer/monoolein type) as specified. Where no specific poloxamer is indicated, poloxamer 407 was used.

Typical examples of the compositions prepared by this method are:

| "8% P407":   | Monoolein:    | 1.15 g   | 4.6%  |
|              | Poloxamer 407:| 0.10 g   | 0.4%  |
|              | Water:        | 23.75 g  | 95.0% |
| "12% P407":  | Monoolein:    | 1.10 g   | 4.4%  |
|              | Poloxamer 407:| 0.15 g   | 0.6%  |
|              | Water:        | 23.75 g  | 95.0% |
| "8.75% P188":| Monoolein:    | 1.1406 g | 4.6%  |
|              | Poloxamer 188:| 0.1094 g | 0.4%  |
|              | Water:        | 23.75 g  | 95.0% |

Example 2

Phase Analysis of Dispersion without Heat Treatment

A dispersion was prepared with Rylo MG19 and 12% poloxamer 407 (referring to the sum of monoolein and poloxamer). The resulting system was a slightly translucent homogenous dispersion, had particle sizes mainly around 0.09 μm (plus small amounts of particles around 0.3 μm) and displayed only extremely weak, unassignable SAXS reflections. By Cryo-TEM, mainly small, lamellar particles were observed with a small proportion of non-lamellar particles (see FIG. 3). The smallest particles were all lamellar, but of the larger particles some displayed internal structure (possibly cubic) and some did not.

Example 3

Effect of Heat Treatment

A freshly prepared dispersion containing Rylo MG19 as monoolein and 12% poloxamer P407 was divided into two fractions. One fraction was autoclaved (121° C., 15 min (plus an equilibration time of 5 min, noted in the following as "(+5 min)", if applied)) and compared to the non-autoclaved fraction. The non-autoclaved fraction was comparable to Example 2, i.e. an slightly translucent homogenous dispersion with particle sizes mainly around 0.09 μm (plus a small number of particles around 0.3 μm) (FIG. 1) and no SAXS reflections. The heat-treated fraction was milky-white (non-transparent) and LS+PIDS analysis (FIG. 1) gave a narrow monomodal particle size distribution (around 0.27 μm, without a smaller particle size fraction). Clear SAXS reflections could be observed for the heat treated sample indicating the presence of cubic P phase. This indicates that the small non-cubic particles in the 0.1 μm range form larger, cubic particles in the medium sized range (ca. 0.3 μm) during the autoclaving process.

Cryo-TEM was performed on autoclaved fraction and compared to Example 2. Only a few small non-cubic particles could be detected after heat treatment. Most of the detectable particles are cubic and in the range of ca. 200-300 nm (FIG. 4). This result is in agreement with the SAXS- and LD+PIDS results of these dispersions: no cubic reflections and a particle size maximum at ca. 0.09 μm in the case of the non-autoclaved dispersion, reflections according to cubic phase type P and a particle size maximum at ca. 0.27 μm in the case of the autoclaved dispersion.

Figure 2:
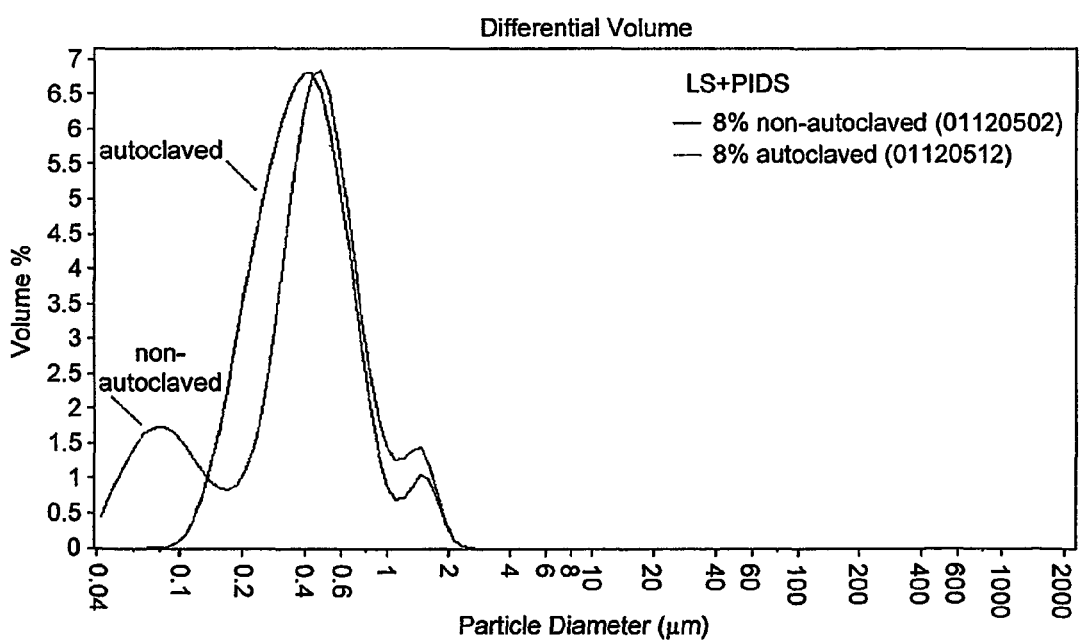
FIG. 2 shows the particle size distribution of a sample of GMO with 8% poloxamer before and after heat treatment.

Similar behaviour was observed for a dispersion containing 8% poloxamer. In this case, the non-autoclaved dispersion is already milky white and displays SAXS reflections (cubic P); the main particle size is in the range of 0.5 μm besides lesser amounts in the range of 0.1 μm and 1.5 μm. Like in the dispersion with 12% poloxamer, aggregates become observable by LM after autoclaving, the small particles vanished and the amount of particles in the medium range increased in LD+PIDS analysis (FIG. 2).

Example 4

Effect of Filtration

Four dispersions were prepared with 12% poloxamer, two of them with GMOrphic-80, the others with Rylo MG 19; In the case of GMOrphic, high pressure homogenization also led to slightly translucent dispersions, similar to previous experiments using Rylo. Fractions of these dispersions were filtered through a 0.45 μm membrane filter (filtration can easily be done by hand using a syringe) without any change in macroscopic appearance. The maximum particle size detected by LM was slightly reduced. LD+PIDS give the same results for the filtered and the unfiltered dispersions, and SAXS reflections cannot be detected in any dispersion.

Samples of the filtered and unfiltered fractions were autoclaved (121° C., 15(+5) minutes). In the filtered and the unfiltered cases, milky white dispersions were obtained with macroscopically visible particles. As in the case of the non-autoclaved dispersions, no clear differences can be detected between the filtered and the not filtered dispersions after autoclaving.

Example 5

Effect of Heat Treatment Time

Figure 5:
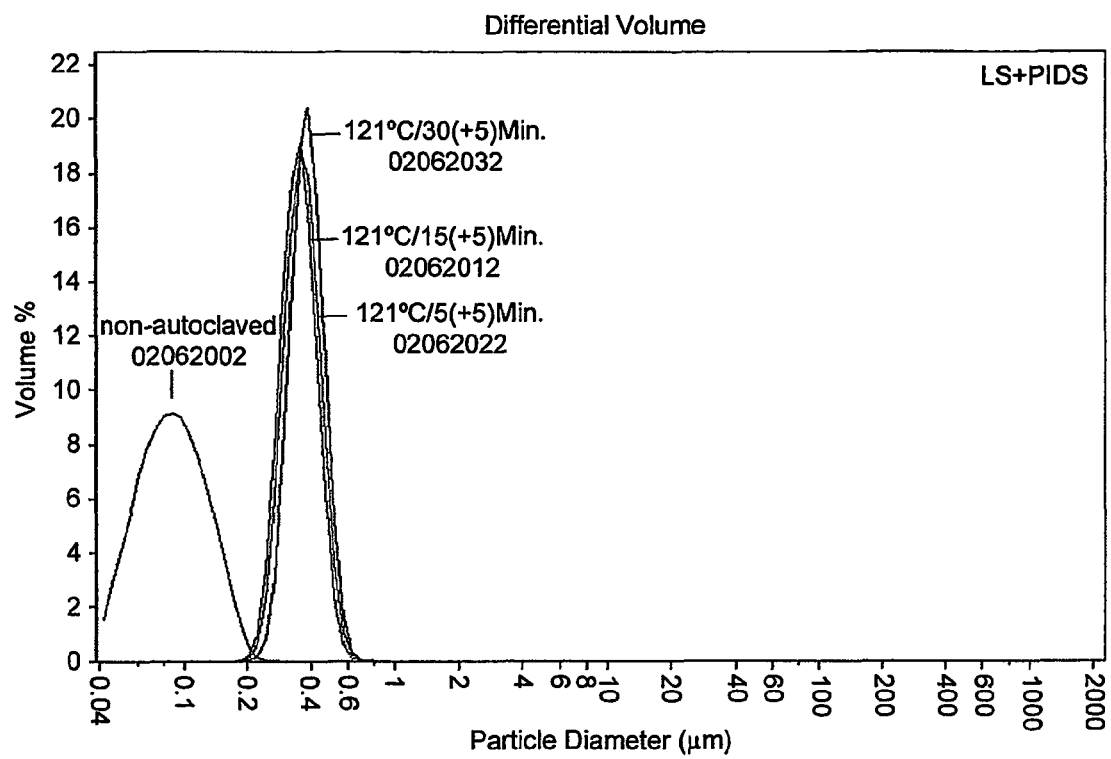
FIG. 5 shows the particle size of a sample before and after heat treatment for various periods.

A dispersion containing Myverol 18-99 as monoolein and 12% poloxamer was divided into four fractions. Three fractions were autoclaved at 121° C. for different periods of time (5 min, 15 min (+5 min), 30 min (+5 min)) and compared to the fourth, non-autoclaved fraction. During autoclaving, the slightly translucent dispersion turned to milky white and visible aggregates appeared. In SAXS, the autoclaved dispersions display diffraction patterns according to the cubic P phase. In the case of the non-autoclaved dispersion no reflections can be detected, not even by the use of synchrotron radiation. LD+PIDS give monomodal particle size distributions for all dispersions, with a mode at ca. 360 to 390 nm for the autoclaved dispersions and a mode at ca. 88 nm for the non-autoclaved dispersion (FIG. 5). There are no detectable differences by any applied method between the autoclaved dispersions. Autoclaving time has thus no significant effect on the properties of the resulting dispersions in the range from 5 to 30(+5) minutes at this temperature.

Example 6

Influence of Temperature

Figure 6:
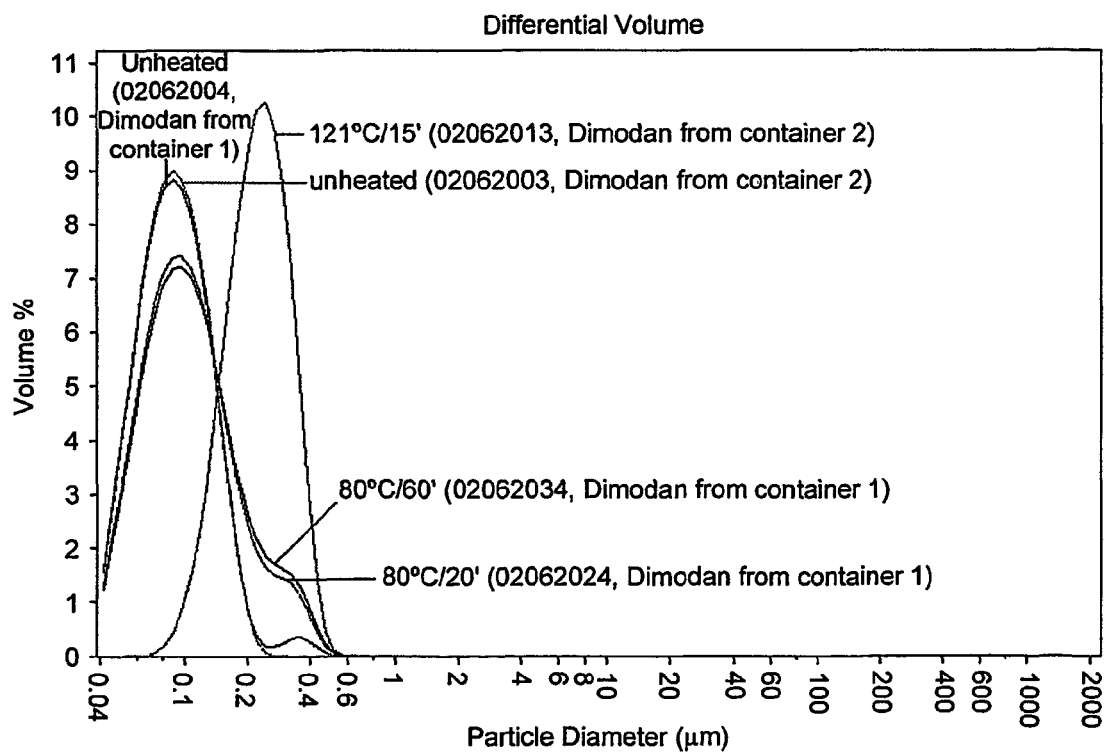
FIG. 6 shows the particle size distribution of samples before and after heating to 80° C. and 121° C.

A dispersion containing Dimodan distilled-GMO as monoolein was divided into four fractions. Two fractions were heated to 80° C. for different periods of time (20 min and 60 min), one fraction was autoclaved (121° C./15(+5) min) and one fraction was left unchanged. Autoclaving changed the dispersion from slightly translucent to milky white, heating to 80° C. led to nearly milky white dispersions (very slightly opaque) in both cases. The LD+PIDS results indicate that the particle size distributions slightly shifted to larger particles during heating to 80° C. (FIG. 6); there is no difference between the two 80° C.-dispersions (20 min and 60 min). A second dispersion with Dimodan from a different container (container 2, same batch) showed nearly the same particle size distribution in the unheated case (the small peak at about 0.35 μm in the dispersion from container 1 is the averaging result of a bigger peak in one measurement run of five, the other runs showed the same particle size distribution as the dispersion from container 2), and increased particle sizes after autoclaving. Compared to autoclaving at 121° C., heating the dispersions to 80° C. led to minor changes in particle size distribution (by means of LD+PIDS). In this case it therefore appears that temperatures higher than 80° C. are necessary to form the large proportions of non-lamellar particles.

Example 7

Influence of Monoolein Type

Autoclaving (121° C./15 min (+5 min)) dispersions containing 12% Poloxamer with GMOrphic-80 or Myverol 18-99, respectively, as monoolein leads to particle size distributions in a similar range. Also the particle size distributions of the corresponding non-autoclaved dispersions are comparable with each other. Even though the use of Dimodan distilled-GMO leads to similar non-autoclaved dispersions, autoclaving of these dispersions leads to different, smaller particle sizes.

Example 8

SAXS Experiments

SAXS experiments on the dispersions of the previous examples were performed. Generally the unheated/non-autoclaved dispersions containing 12% poloxamer did not display X-ray reflections and only in a few cases were extremely weak, unassignable reflections observed. The heated dispersions (80° C.: 20 min and 60 min) display very weak reflections due to cubic P phase. In the case of the autoclaved dispersions (121° C., 5 min, 15 min and 30 min), weak reflections for the Dimodan dispersions and clear reflections for the GMOrphic and Myverol dispersions were obtained, all pointing to cubic P phase.

Example 9

Further Influence of Temperature

Figure 7:
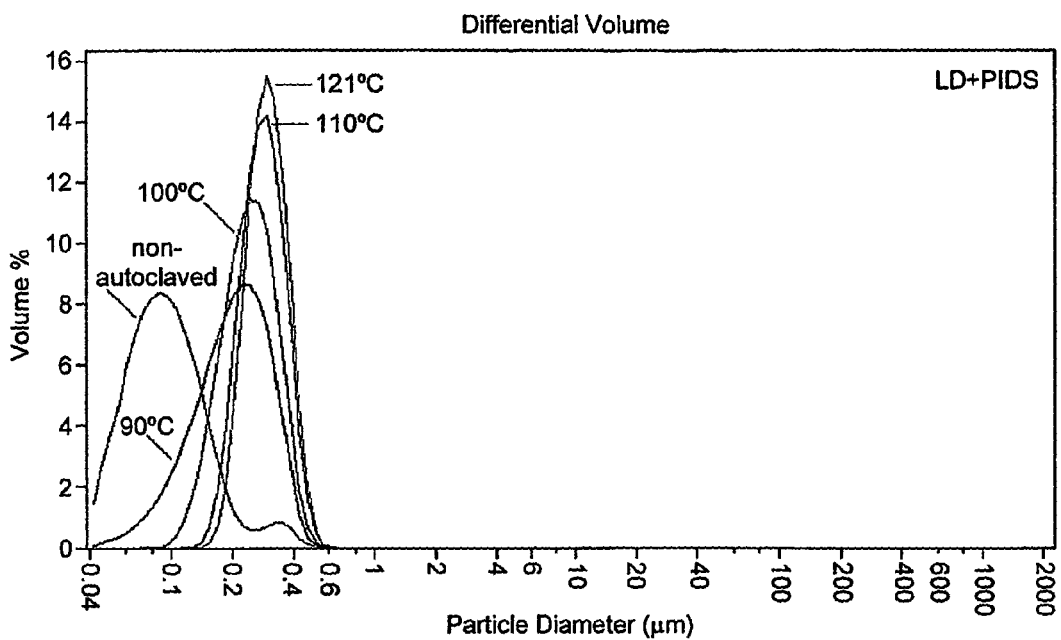
FIG. 7 shows the particle size distribution of a sample before and after heat treatment at various temperatures.

For further investigation of the influence of the temperature applied during the heating process after homogenization, a dispersion containing GMOrphic-80 as monoolein (MO) and 12% P407 (based on the sum of MO and P407) was prepared according to the standard procedure (Example 1). Fractions of the homogenized dispersion were heated to 90° C., 100° C., 110° C. and 121° C., respectively, for 20 minutes, and compared to a non-heated fraction (FIG. 7).

With increasing temperature, the mean particle size increases and the PSD becomes narrower. There is only a weak difference in the results obtained after heating to 110° C. and 121° C., which lead to the assumption that heating to higher temperatures than 121° C. will probably not result in a narrower PSD. After heating to 90° C., ca. 50% of the particles were larger than 0.2 μm and clear SAXS reflections (cubic P) were observed, in contrast to the result after heating to 80° C. (see Example 6), where 90% of the particles remained smaller than 0.2 μm and only very weak SAXS reflections (probably cubic P) were detected. The non-heated fraction and the 121° C./15(+5) min fraction give the usual results obtained earlier. It was concluded that in this case the minimum temperature necessary for PSD narrowing and conversion to non-lamellar particles was in the region of 90° C.

Example 10

Influence of Poloxamer Concentration

Figure 8:
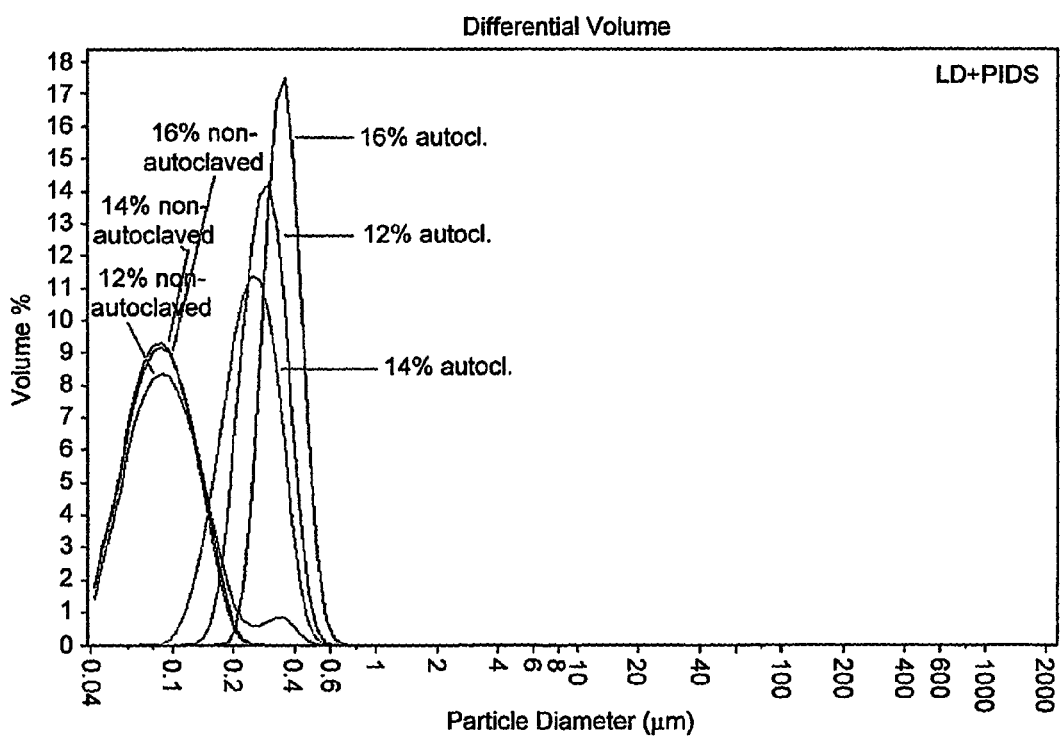
FIG. 8 shows the effect of heat treatment at varying poloxamer concentrations.

For testing the influence of poloxamer 407 concentrations above 12% on the effect of autoclaving, dispersions containing 12%, 14% and 16% P407 were prepared according to the standard procedure. Fractions of these dispersions were autoclaved (121° C./15(+5) min) and compared to the non-autoclaved fractions (FIG. 8).

In both cases (autoclaved and non-autoclaved), no difference can be detected between the 12% dispersion and the dispersions with higher concentrations of P407 by visual inspection, light microscopy and SAXS. All of the non-autoclaved dispersions were slightly translucent and displayed no SAXS reflections. After autoclaving, they turned into milky-white dispersions with large aggregates, and displayed clear SAXS reflections according to cubic P with nearly the same lattice constants.

The LD+PIDS results demonstrate that increasing the P407-concentration from 12% to 14% slightly reduces the fraction of particles in the 0.2-0.5 μm range in the non-autoclaved dispersions. Further increasing of the P407-concentration had no effect on the LD+PIDS result. The mode value and the width of the PSD for the autoclaved dispersion are slightly different for the different P407-concentrations despite the fact that they were autoclaved together by the same autoclaving process. No correlation was seen between P407-concentration and PSD mode value or PSD width.

Example 11

Influence of Poloxamer Type

Figure 9:
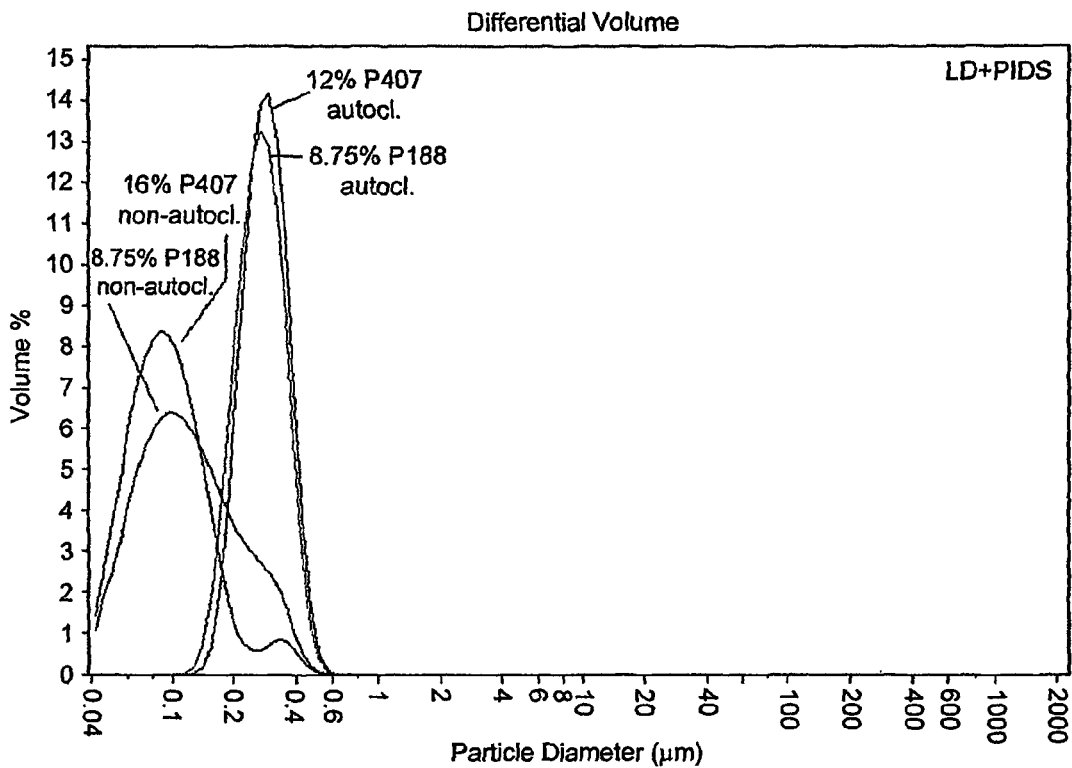
FIG. 9 shows the effect of heat treatment of compositions containing two different poloxamer types.

To test the influence of the poloxamer type on the properties of the resulting dispersions, poloxamer 188 (P188) was used instead of P407. A dispersion was prepared according to the standard procedure (Example 1) with P188-concentrations of 8.75 weight-% (based on the sum of MO and P188). This concentration of P188 is equivalent (when calculated as mol-%) to the usual concentrations of P407 (12 weight-%). Fractions of this dispersion were autoclaved (121° C./15(+5) min). The dispersion was compared to a non-autoclaved and autoclaved dispersion with 12% P407 (FIG. 9).

Figure 10:
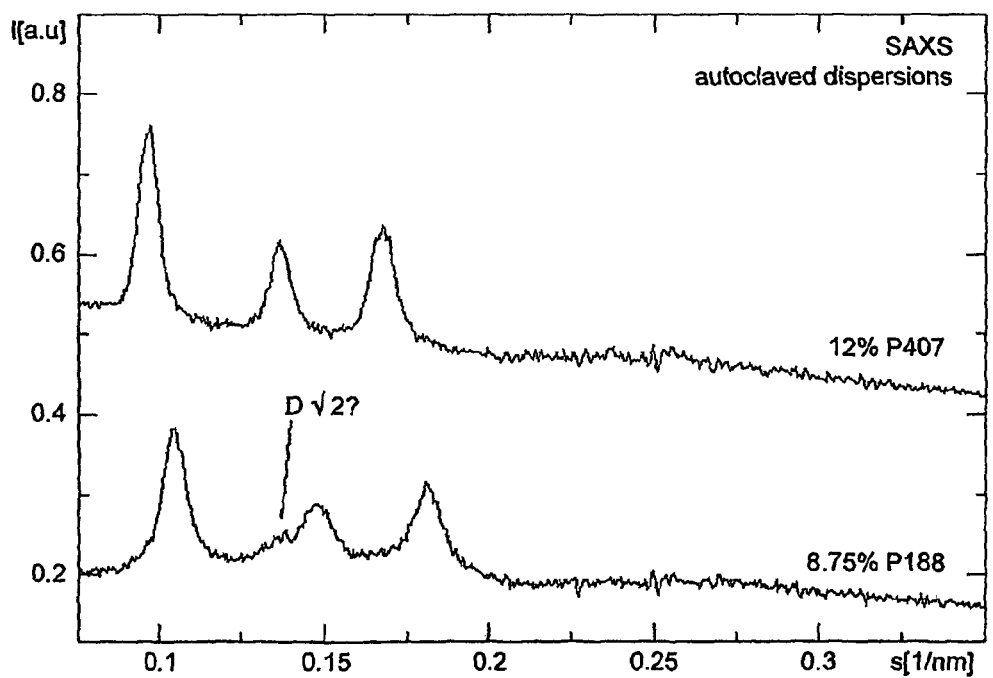
FIG. 10 shows small angle X-ray scattering (SAXS) patterns for two samples, containing two different poloxamer types, after heat treatment.

The homogenized (non-autoclaved) dispersion with 8.75% P188 was homogenous and nearly milky white. SAXS reflections were not detected and LD+PIDS displayed a PSD with a slightly higher amount of particles in the size range of ca. 0.2-0.5 μm compared to the non-autoclaved dispersion with 12% P407. The autoclaved fraction of this dispersion was milky-white with large aggregates and displayed clear cubic P SAXS reflections, like the autoclaved dispersion with 12% P407 do (see FIG. 10). A very weak peak in the autoclaved 8.75% P188-dispersion between the first and the second cubic P reflection is in the region where the first reflection of a cubic D phase would be expected and may indicate a small amount of cubic D phase in this dispersion. The lattice constant (of the cubic P phase) is smaller in the case of the dispersion containing 8.75% P188 (ca. 13.5 nm) compared to that of the dispersion containing 12% P407 (ca. 14.4 nm). The PSD (LD+PIDS) was nearly the same as that of the autoclaved dispersion with 12% P407.

Example 12

Influence of Long-Term Storage

Figure 11:
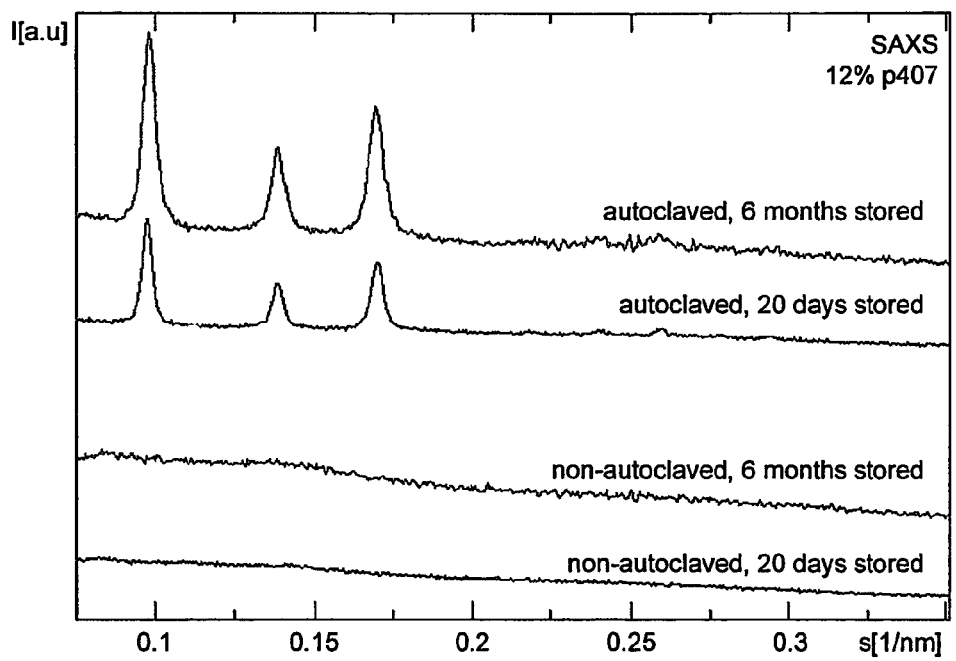
FIG. 11 shows the effect of storage on the SAXS for samples with and without heat treatment (curves after 20 days and 6 months are not on the same scale)

To answer the question, whether the lamellar particles of a non-autoclaved dispersion with 12% P407 transform into non-lamellar particles with time without heat treatment, or whether the cubic particles produced by autoclaving a dispersion with 12% P407 transform back to lamellar particles with time, dispersions (12% P407, non-autoclaved and autoclaved) were investigated by SAXS after a storage period of 6 months (at 23° C., called "stored dispersions") after preparation. The results were compared to the SAXS results of these dispersions obtained 20 days (stored at 23° C., called "unstored dispersions") after preparation (FIG. 11).

In the case of the autoclaved dispersion, the diffractograms of both dispersions (stored and unstored) display clear cubic P reflections, the lattice constants are the same (14.4 nm). No additional reflections occur after storage (a phase change to cubic D or hexagonal with time, possibly caused by, e.g., hydrolysis of the monoolein, would result in additional reflections).

In the case of the non-autoclaved dispersion, there are no reflections detectable in the diffractograms of either system. The result, that no detectable cubic P phase is formed in non-autoclaved dispersions (with 12% P407) by time, was confirmed by examination of a second, independent batch (after 7 days and 6 months after preparation).

Example 13

Influence of Drug Loading

Five different drugs (ubidecarenone, tocopherol acetate, miconazole, betamethasone-17-valerate, chloramphenicol) were incorporated in a monoolein (GMOrphic) dispersion stabilized with 12% P407 (which forms a lamellar vesicular dispersion in the unloaded state) by adding the drugs to the MO/P407 melt at 60° C. (or 80° C. for concentrations of 5% drug) in the "standard" preparation process (see Example 1). All drug concentrations are indicated relative to the sum of monoglyceride and poloxamer. A drug-free dispersion was prepared and investigated as a reference.

All dispersions were autoclaved at 121° C. for 15+5 min. (allowing for temperature equilibration in the autoclave) and their properties were compared to that of the corresponding non-autoclaved dispersions.

Ubidecarenone and tocopherol acetate at a concentration of 0.3% did not influence the properties of the resulting dispersions. The transformation of lamellar vesicular into non-lamellar (cubic) particles upon autoclaving proceeded as in the drug-free dispersions. Higher concentrations of these drugs were not investigated.

Dispersions with 0.3, 1 or 2% betamethasone-17-valerate also had no influence on the general behaviour of the dispersions. A drug load of 5% could not be realized with this substance since it could not be dissolved in the MO/P407 melt at this concentration.

Chloramphenicol at 0.3, 1 and 2% as well as miconazole at 0.3 and 1% had no influence on the non-autoclaved dispersions. In autoclaved dispersions, however, a concentration dependent influence could be observed: In chloramphenicol-loaded dispersions the particle sizes increased distinctly with drug concentration and a slight increase in lattice constant of the cubic phase was observed. 5% chloramphenicol could be incorporated in the MO-dispersion but homogenization as well as autoclaving led to dispersions with distinctly larger particle sizes in comparison to the drug free dispersions and those with up to 2% drug.

For the 5% chloramphenicol sample, cubic reflections could be observed in small angle X-ray scattering even before autoclaving. The lattice constant of the cubic phase in the (non-autoclaved and autoclaved) 5% sample is much larger than in the autoclaved drug-free dispersion or (autoclaved) dispersions with up to 2% chloramphenicol.

Miconazole could be incorporated at concentrations of 0.3 and 1%. Homogenization of these dispersions led to opaque dispersions without cubic X-ray reflections in all cases. Autoclaving led to slightly larger (0.3%) and distinctly larger (1%) particle sizes compared to the dispersions without drug incorporation. The lattice constant decreased slightly.

Example 14

Autoclaving of a Liposomal Dispersion

In order to assess whether a standard liposomal dispersion having a lamellar equilibrium form at room temperature would convert to non-lamellar particles under heating, the method was tested on a liposomal dispersion.

To prepare the liposomal dispersion, 5% egg phospholipid (Lipoid E80) was stirred in water (containing 0.01% thiomersal as a preservative) for one day at room temperature and subsequently extruded (Avestin Emulsiflex-C5) 10 times through a 100 nm polycarbonate filter. The resulting dispersion had a PCS z-average diameter of 117 nm with a polydispersity index of 0.08.

Figure 12:
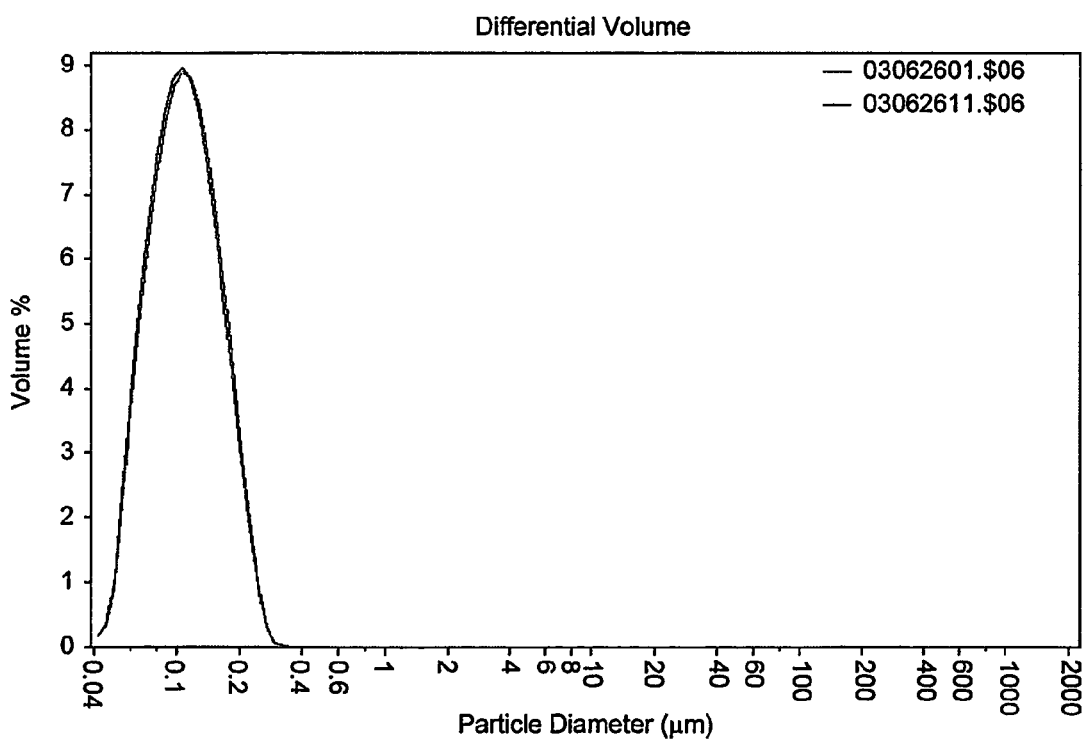
FIG. 12 shows the comparative effect of heat treatment on the particle size distribution of a liposomal sample.
Figure 13:
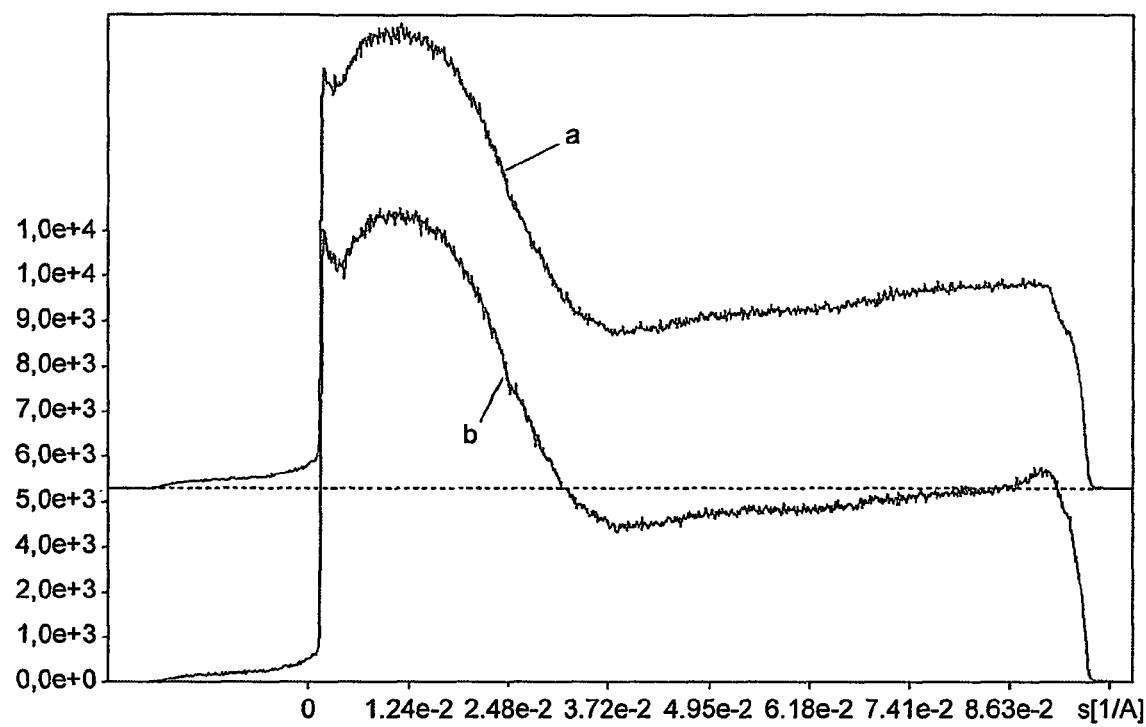
FIG. 13 shows the comparative effect of heat treatment on the SAX pattern of a liposomal sample.

One fraction of the dispersion was autoclaved for 15+5 min. at 121° C. and the properties of the resulting dispersion were compared to that of the non-autoclaved one. Except for slight differences in optical appearance no differences between the two samples were observed with the following methods:

Both samples are visually homogenous without macroscopically detectable particles and of yellowish-opaque appearance with a slightly more intense colour after autoclaving. The particle size measurement with laser diffraction+PIDS yields a monomodal particle size distribution with a mode at 106 nm for both dispersions (FIG. 12). Both dispersions display diffuse small angle X-ray scattering without detectable sharp reflections, indicating the presence of only lamellar particles (FIG. 13 a) before heating b) after heat treatment).

Example 15

Compositions Including Fatty Acids

Figure 14:
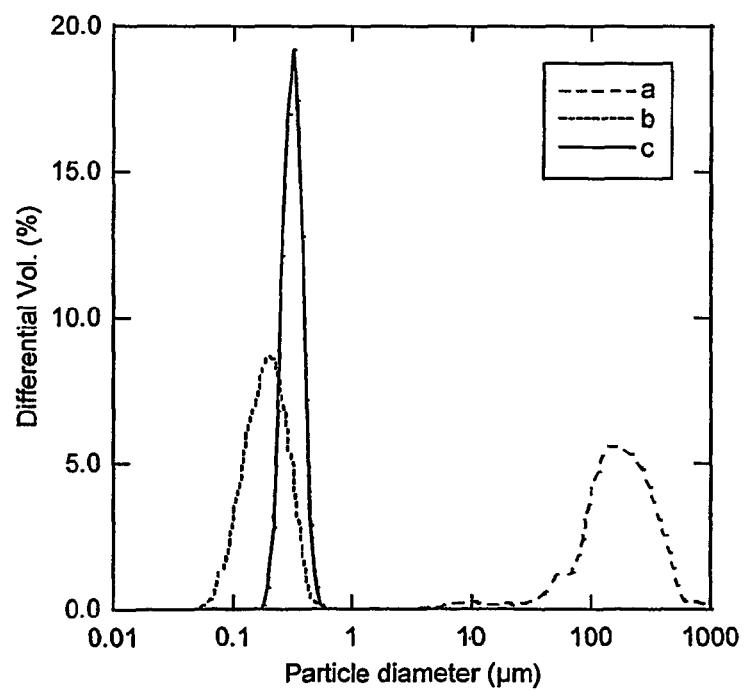
FIG. 14 shows the particle size distribution of a composition of GMO, poloxamer and oleic acid before and after heat cycling.

Pre-formulations were prepared using the standard method indicated in Example 1 but including the fatty acid oleic acid in the formulation.

a) An initial melt was prepared containing GMO (85.5%), oleic acid (4.5%) and Lutrol F127 (10%). To 9 g of water under mechanical stirring was added 1 g of the molten mixture to form a coarse dispersion. This was examined for phase structure and comprised principally cubic liquid crystalline phase particles of average diameter greater than 100 μm. The particle size distribution of the coarse dispersion is shown as "a" in FIGS. 14 and 15.

b) The coarse dispersion was divided into two portions. The first portion was homogenised with the microfluidiser at 345 bar and the second portion homogenised with the microfluidiser at 172 bar. The particle size distributions of the two resulting dispersions are indicated as "b" in FIGS. 14 and 15 respectively. It can be seen that higher pressure homogenisation gave a mono-modal particle size distribution of relatively small particles and lower pressure homogenisation gave larger particles with a bimodal distribution.

c) The two dispersions prepared in part b) were each heated to 120° C. for 20 minutes and the particle phase and size distributions reexamined. The results indicated largely cubic liquid crystal particles with size distributions as indicated as "c" in FIGS. 14 and 15. The maximum particle sizes remained essentially static but the width of the distribution decreased notably in the case of the low pressure homogenisation (FIG. 15) and remarkably in the case of the high pressure homogenisation (FIG. 14).

After heat cycling, both compositions were of colloidal particles and had sharp, narrow particle size distributions. Such dispersions are thus highly suitable for both intravenous administration and controlled release applications by any suitable administration route.

Example 16

Storage Stability

The dispersions prepared in Example 15 parts (b) (before heat treatment) and (c) (after heat treatment) resulting from high pressure homogenisation were stored for 11 days at room temperature. After storage the particle size distribution was again examined and is indicated in FIG. 16.

Figure 16:
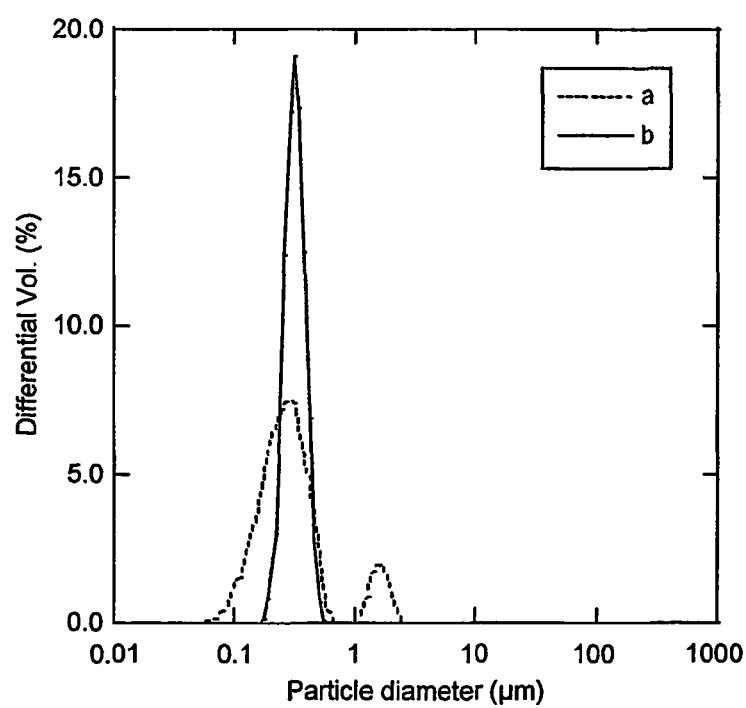
FIG. 16 shows the particle size distribution of a composition of GMO, poloxamer and oleic acid with and without heat cycling after 11 days' storage.

The effects of storage on particle size may be seen by comparing FIGS. 14 and 16. It can be seen that the non-heat treated sample ("a" in FIG. 16) increased somewhat in mode particle size and showed a bimodal distribution after storage, with a secondary portion of particles above 1 μm in diameter. In contrast, the heat treated sample ("b" in FIG. 16) shows a distribution of particles indistinguishable from that prior to storage ("c" in FIG. 14). Thus, the heat treatment cycle not only narrowed the particle size distribution of the sample but also rendered the sample more stable to storage.

Example 17

Ternary Non-Lamellar Particles 17.1—Preparation of a Non-Lamellar Dispersion A coarse dispersion of cubic and lamellar particles was formed by mixing DOPE (Avanti Polar Lipids U.S.A., 0.75 g), TMGO-15 (Nikko Japan, 0.2 g) and DOPE-PEG(5000) (Avanti Polar Lipids U.S.A., 0.05 g) in deionized water (49.0 g). The mixture was freeze-thawed 3 times including freezing at −85° C. and thawing under vigorous stirring and shaking at ambient temperature. The resulting coarse dispersion was thereafter homogenised in a microfluidizer at high pressure (350 bar) for 10 min (8 passes) at ambient temperature.

The particle size was measured using laser diffraction (Coulter LS230) after homogenisation.

The homogenised sample was a turbid to bluish colloidal dispersion with particle sizes between 0.05 and 1 micron consisting of cubic phase particles and vesicles.

17.2—Heat Treatment

A cycle of heat treatment was carried out on the dispersion prepared in Example 17.1.

A sample of the dispersion generated in Example 17.1 (25 mL) was autoclaved (120° C., 20 min) and cooled to room temperature. When examined by cryo-TEM, a still greater proportion of the particles in the dispersion showed non-lamellar character. The particle size distribution was also somewhat narrowed in comparison with the dispersion prior to heat treatment and shows better storage stability.

Components:
a DOPE
b TMGO-15 (glycerylmonooleate-PEG(15), Nikko, Japan)
c DOPE-PEG(5000)

| Formulation | a:b:c | abc wt % | aqueous medium | aq wt % | Phase before | Temp ° C. | Time min | Phase after |
|---|---|---|---|---|---|---|---|---|
| i | 75:20:5 | 2 | water | 98 | lam/cubic* | 120 | 20 | cubic** |

Figure 17:
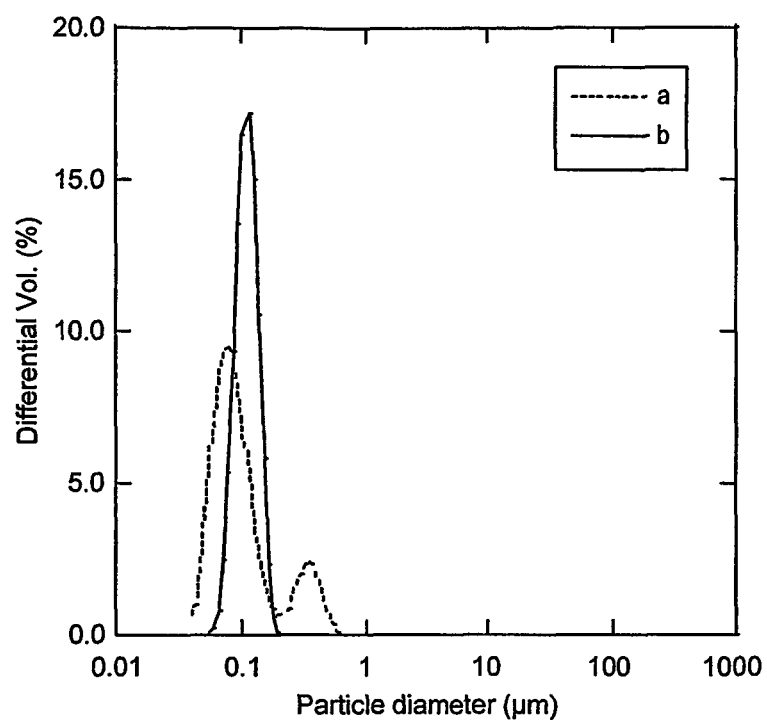
FIG. 17 shows the effect of Heat Treatment on the particle size distribution of a DOPE/TMGO-15/DOPE-PEG(5000) ternary composition.

*lam/cubic = mixed cubic and lamellar particles
**cubic = predominantly cubic particles The particle size distribution of the composition before and after heat treatment is shown in FIG. 17.

Example 18

Effect of Controlled Ionic Strength

The effect of ionic strength during heat treatment was considered by preparing a second composition by the methods of Examples 17.1 and 17.2. The same components a, b and c were used but at a different weight ratio and 3 mM NaCl was used in place of water for the heat treatment step.

| Formulation | a:b:c | abc wt % | aqueous medium | aq wt % | Phase before | Temp ° C. | Time min | Phase after |
|---|---|---|---|---|---|---|---|---|
| ii | 77.2:20.3:2.5 | 2 | 3 mM NaCl | 98 | lam/cubic* | 120 | 20 | cubic* |

Figure 18:
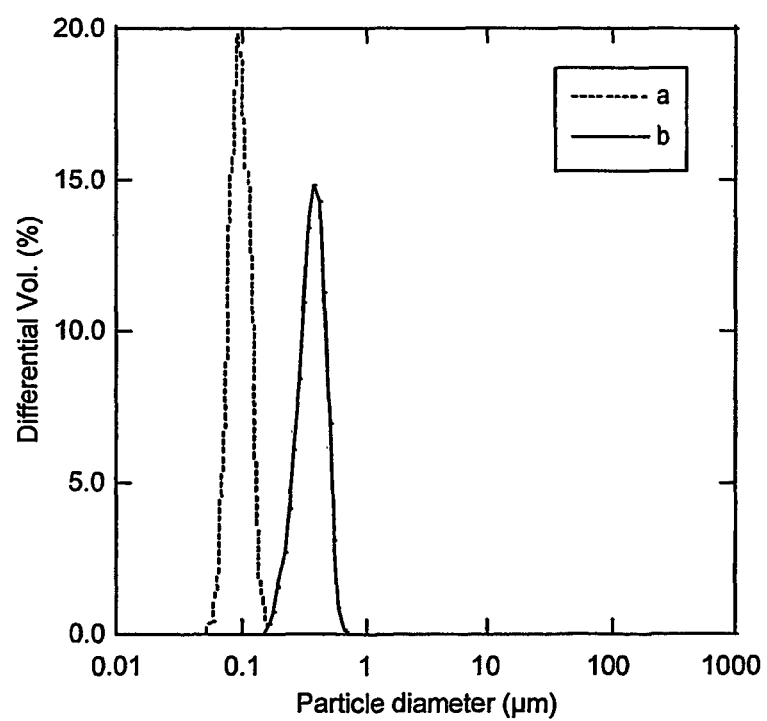
FIG. 18 shows the effect of Heat Treatment on the particle size distribution of a DOPE/TMGO-15/DOPE-PEG(5000) ternary composition in 3 mM NaCl.

The particle size distribution before and after heat treatment is indicated in FIG. 18. In this case, the effect of the higher ionic strength is seen to cause the mode particle size to increase around four-fold while maintaining a narrow particle size distribution. The particles were also converted to essentially 100% cubic phase particles.

Example 19

Further Ternary Composition

Figure 19:
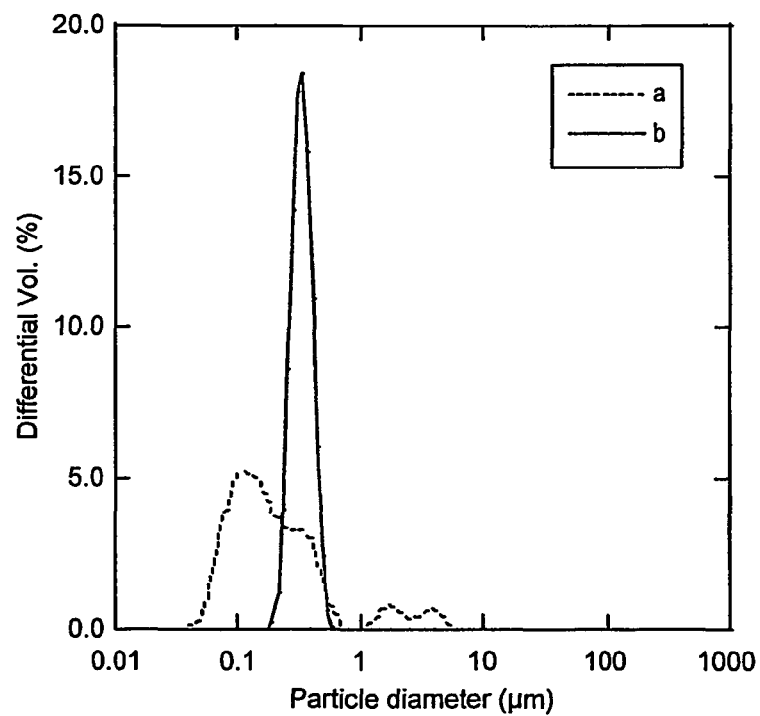
FIG. 19 shows the effect of Heat Treatment on the particle size distribution of a DOPE/P80/Pluronic F127 ternary composition.

A dispersion of DOPE (0.80 g), Polysorbate 80 (0.134 g) and Pluronic® F127 (0.10 g) in deionized water (49.0 g) was prepared by the methods of Examples 17.1 and 17.2. The particle size distribution measured before and after heat treatment is indicated in FIG. 19. The heat treatment is seen to transform the original particles exhibiting a broad multi-modal size distribution into particles with a mono-modal narrow size distribution. The proportion of cubic phase particles in the dispersion was increased to nearly 100% after the heat treatment.

Components:
a DOPE
b Polysorbate 80
c Pluronic® F127

| Formulation | a:b:c | abc wt % | aqueous medium | aq wt % | Phase before | Temp ° C. | Time min | Phase after |
|---|---|---|---|---|---|---|---|---|
| iii | 77.4:13.0:9.6 | 2 | water | 98 | lam/cubic* | 120 | 20 | cubic* |

Example 20

Charged Ternary/Quaternary Compositions

Compositions including a charged amphiphile in component a were prepared.

Figure 20:
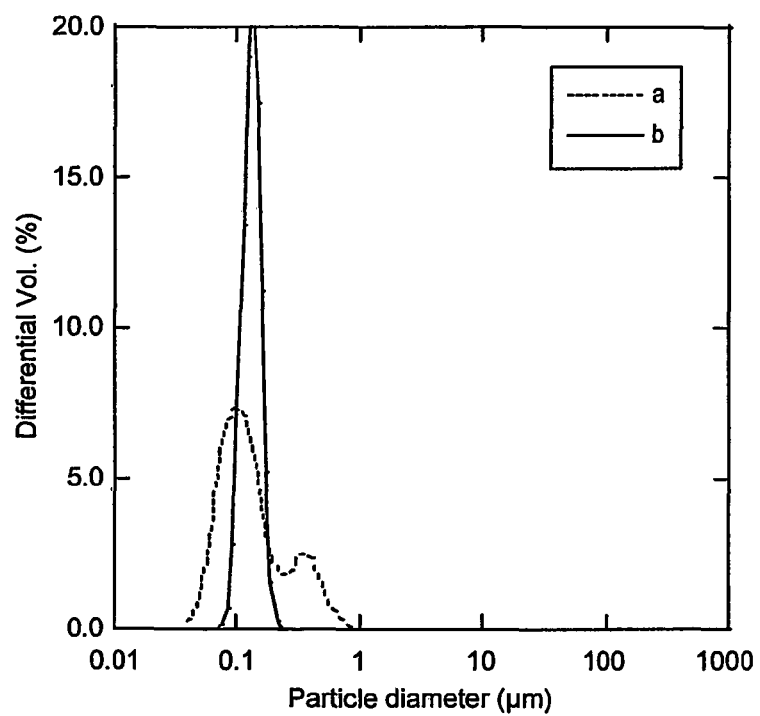
FIG. 20 shows the effect of Heat Treatment on the particle size distribution of a DOPE:DOPG/TMGO-15/DOPE-PEG (5000) four-component composition.

A dispersion of DOPE (0.90 g), DOPG (0.036 g), TMGO-15 (0.207 g) and DOPE-PEG(5000) (0.06 g) in deionized water (58.8 g) was prepared by the methods of Examples 17.1 and 17.2. The heat treatment was performed in 5 mM NaCl resulting in a mono-modal narrow size distribution. The particle size distribution measured before and after heat treatment is indicated in FIG. 20. The heat treatment was also accompanied by a turbidity increase of the sample indicating that a greater proportion of the particles in the dispersion were of non-lamellar character.

Components:
a1 DOPE
a2 DOPG
b TMGO-15
c DOPE-PEG(5000)

| Formulation | a1:a2:b:c | abc wt % | aqueous medium | aq wt % | Phase before | Temp ° C. | Time min | Phase after |
|---|---|---|---|---|---|---|---|---|
| iv | 75:3:17:5 | 2 | 5 mM NaCl | 98 | lam/cubic* | 120 | 20 | cubic** |

Example 21

Further Charged Composition

Figure 21:
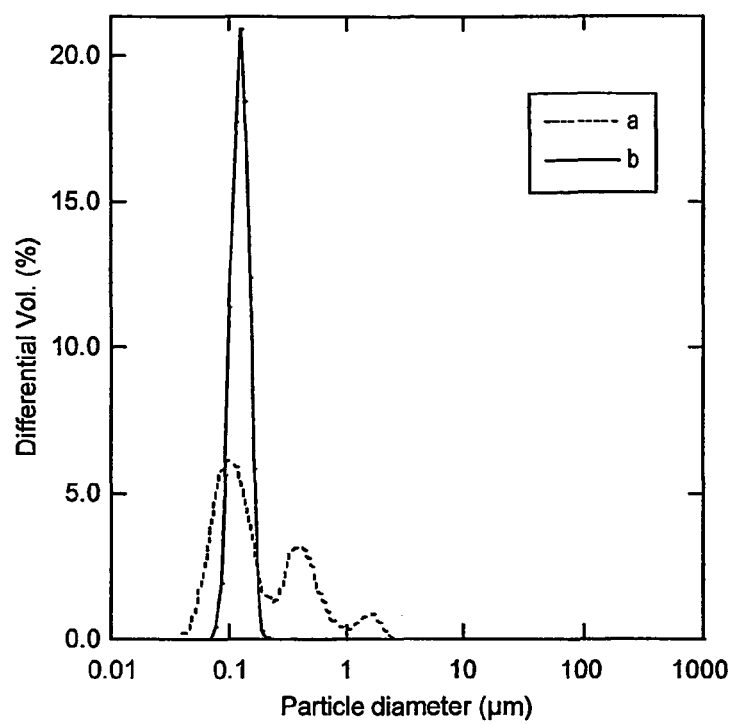
FIG. 21 shows the effect of Heat Treatment on the particle size distribution of a DOPE:DOPG/P80/DOPE-PEG(5000) four-component composition.

A dispersion of DOPE (0.90 g), DOPG (0.036 g), Polysorbate 80 (0.212 g) and DOPE-PEG(5000) (0.06 g) in deionized water (58.8 g) was prepared by the methods of Examples 17.1 and 17.2. The heat treatment was performed in 5 mM NaCl resulting in a mono-modal narrow size distribution. The particle size distribution measured before and after heat treatment is indicated in FIG. 21. A greater proportion of the particles in the dispersion showed non-lamellar character after the heat treatment.

Components:
a1 DOPE
a2 DOPG
b Polysorbate 80
c DOPE-PEG(5000)

| Formulation | a1:a2:b:c | abc wt % | aqueous medium | aq wt % | Phase before | Temp ° C. | Time min | Phase after |
|---|---|---|---|---|---|---|---|---|
| v | 75:3:17:5 | 2 | 5 mM NaCl | 98 | lam/cubic* | 120 | 20 | cubic** |

Example 22

Active Agent Loading

Non-lamellar dispersions of varying components in water and saline solutions may be prepared by the method of Example 17.1 and treated with the heat treatment method of Example 17.2.

To the dispersions is added the cationic peptide desmopressin to a concentration of 1 mg/ml. The dispersion is allowed to equilibrate for 60 minutes at room temperature and reanalyzed for particle size and optionally phase behaviour. The particle size is not affected as determined using laser diffraction.

Example 23

Toxicity Testing 23.1 Hemolysis

Figure 22:
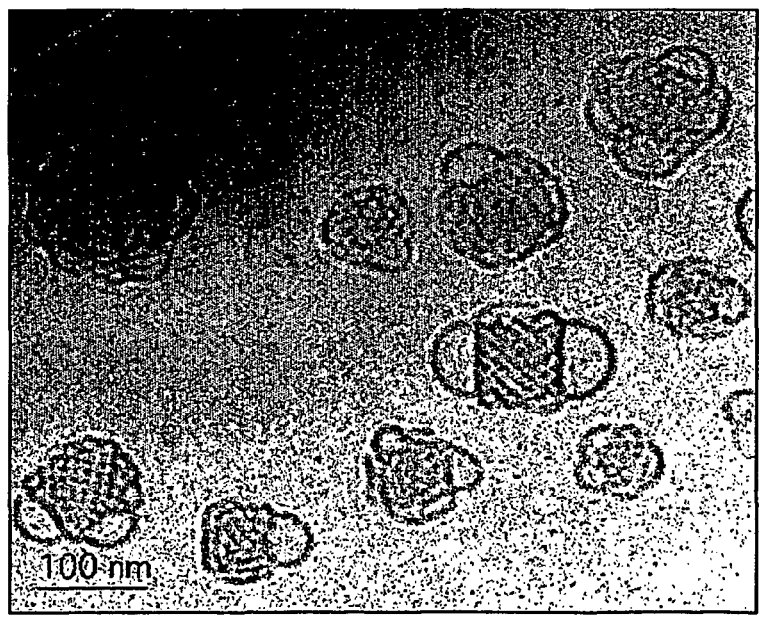
FIG. 22 shows a cryo-TEM image of a DOPE/TMGO-15/DOPE-PPEG(5000) composition, showing the non-lamellar structure of the particles.

A cubic phase dispersion was prepared by the methods of Examples 17.1 and 17.2 using the following components:
a) DOPE
b) TMGO-15
b) DOPE-PEG5000
in the weight ratio a:b:c 76:20:4, dispersed in water to a total amphiphile concentration of 2 wt %. This solution was diluted with water to varying final concentrations. A Cryo-TEM image of the dispersion is shown in FIG. 22.

The hemolytic effect of the cubic phase dispersion at varying concentrations was measured. The dispersion was found to be non-hemolytic at concentrations of up to 1 wt % total amphiphile.

23.2 Pyrogenicity

A DOPE based formulation was prepared as in Example 23.1 and was tested for pyrogenicity in a rabbit model. The composition was found to be non-pyrogenic up to doses of at least 5 ml/kg (5 wt % total amphiphile).

23.3 Acute Toxicity

DOPE based compositions were prepared as in Example 23.1 and tested for acute toxicity in a rat model.

The DOPE based cubic phase dispersion showed no acute toxicity in a dose dependent study with doses up to 10 ml/kg (10 wt % amphiphile).

Example 24

Control of Particle Size by Means of Concentration

Dispersions of GMO/F-127 (90:10) and GMO:OA/F127 (84.5:4.5:9) were prepared as in the above Examples (see especially Examples 1-3 & 15), but was diluted to a known concentration in the aqueous medium prior to homogenisation by Microfluidizer in water (six passes at 345 bar) and heat treatment at 120° C. for 20 minutes followed by annealing at room temperature. In both cases dispersions of cubic phase particles were formed.

The particle size distribution and average particles sizes for the resulting dispersions were analysed as above.

Figure 23A:
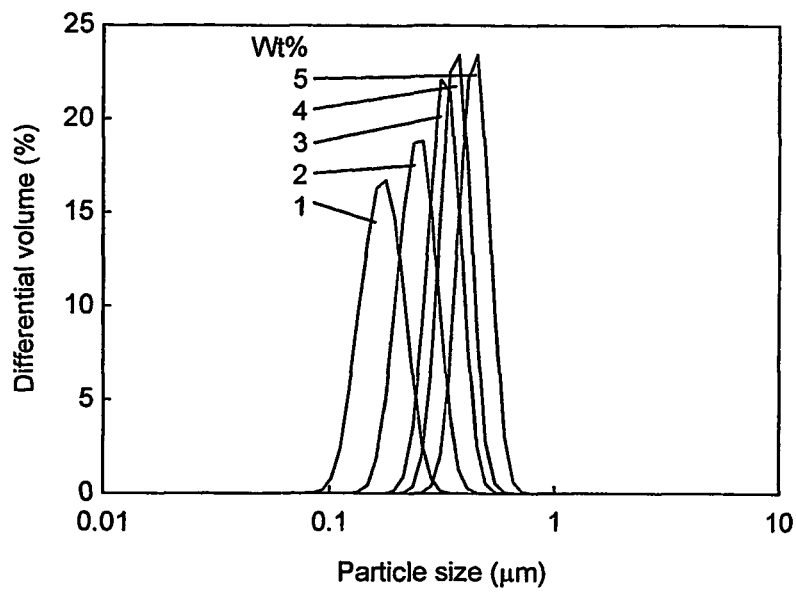
FIG. 23a shows the particle size distribution of a GMO/F127 dispersion heat treated at different concentrations.
Figure 23B:
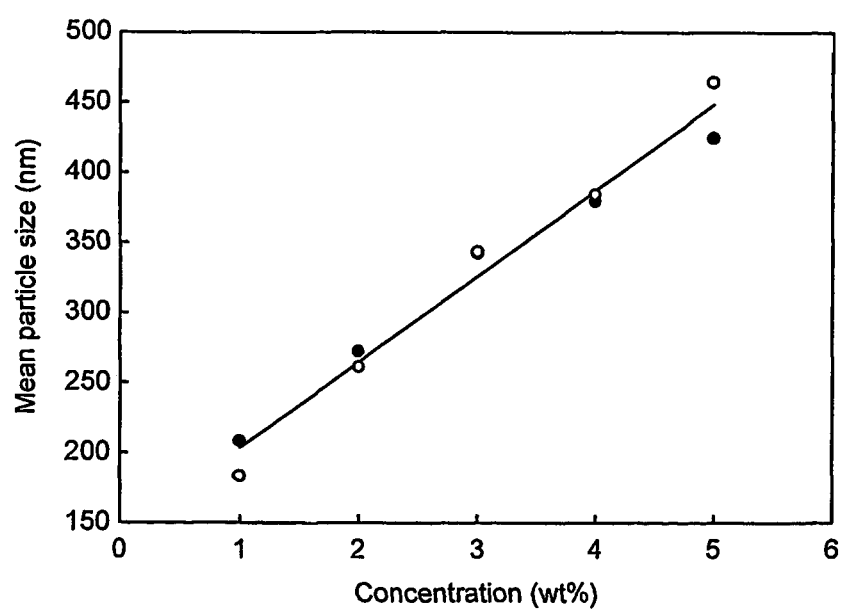
FIG. 23b shows the average particle sizes GMO/F127 dispersions heat treated at different concentrations.

FIG. 23a shows the particle size distributions for GMO/F-127 (90:10) treated at dilutions of 1 to 5 wt % total mixture in water. The corresponding average particles sizes is shown in FIG. 23b.

Figure 24A:
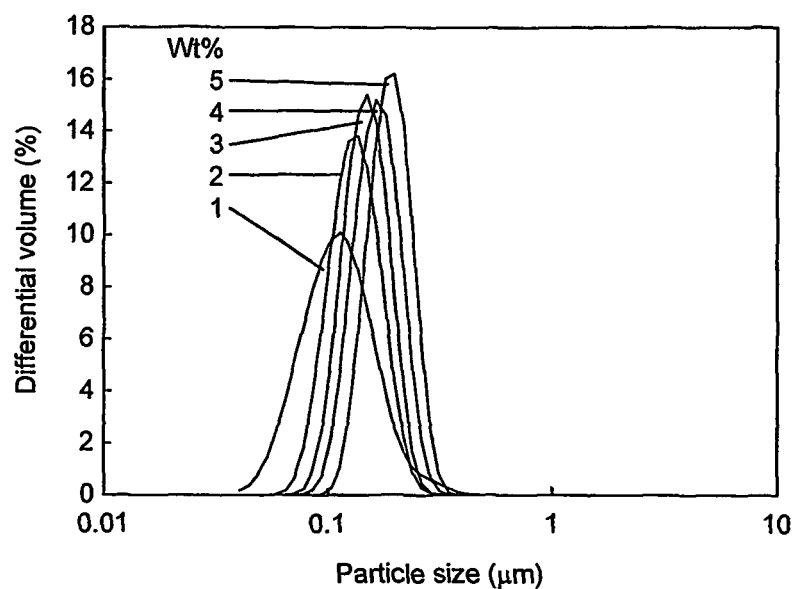
FIG. 24a shows the particle size distribution of a GMO/OA/F127 dispersion heat treated at different concentrations.
Figure 24B:
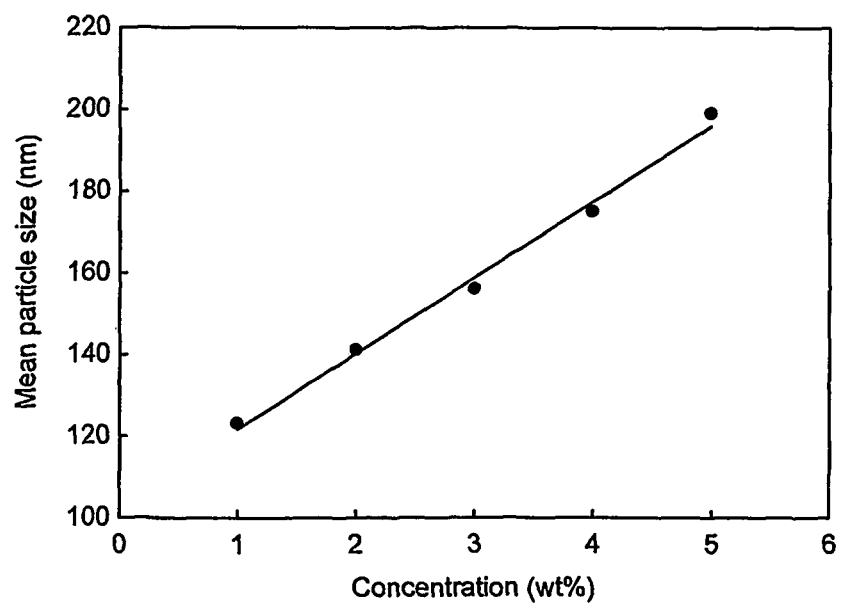
FIG. 24b shows the average particle sizes GMO/OA/F127 dispersions heat treated at different concentrations.

FIG. 24a shows the particle size distributions for GMO/OA/F-127 (84.5:4.5:10) treated at dilutions of 1 to 5 wt % total mixture in water. The corresponding average particles sizes are shown in FIG. 24b.

It can be seen that the average particle size after treatment is directly dependent upon the treatment concentration.

Example 25

Stability of Progesterone to Heat Treatment

The steroid hormone progesterone is dissolved in water at a level of 1% by weight. The solution is subsequently heated to 120° C. in an autoclave for 20 minutes and cooled to room temperature. The solution is concentrated by freeze-drying and the residue analysed for breakdown products by gas chromatography mass spectrometry.

Example 26

Higher Loading by Heat Treatment

A dispersion of cubic particles of formulation GMO/OA/F-127 (84.5:4.5:10) was prepared as in Example 24. The steroid hormone progesterone was incubated with the cubic particles at room temperature as described for desmopressin in Example 22. The equilibrium loading level was 3% by weight.

The above method was repeated by the active agent progesterone was included in the aqueous phase prior to the homogenisation and heat treatment steps. The loading level was again examined and established to be 18 wt %. The effect upon the particle size distribution was minimal.

The composition with 18 wt % progesterone generated above was stored at room temperature for 14 days. No degradation of the composition or decrease in the loading level was observed after this time.

Legend to FIG. 14: Particle-size distribution of liquid crystalline (cubic phase) dispersion after a) mechanical agitation, b) homogenisation by Microfluidizer (six passes) operating at 345 bar, and following c) heating to 120° C. for 20 minutes.

Figure 15:
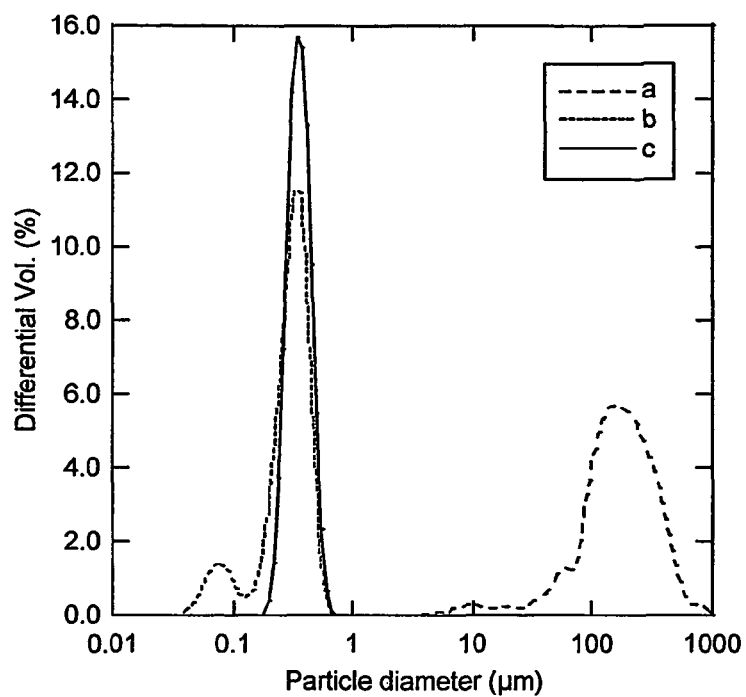
FIG. 15 shows the particle size distribution of a further composition of GMO, poloxamer and oleic acid before and after heat cycling.

Legend to FIG. 15: Particle-size distribution of liquid crystalline (cubic phase) dispersion after a) mechanical agitation, b) homogenisation by Microfluidizer (six passes) operating at 172 bar, and following c) autoclaving 120 C for 20 minutes.

Legend to FIG. 16: Particle-size distribution of liquid crystalline (cubic phase) dispersion after 11 days storage of sample a) homogenised by Microfluidizer (six passes) operating at 345 bar, and following b) heated to 120 C for 20 minutes.

Legend to FIG. 22: Cryo-TEM image of non-lamellar particles obtained after heat-treating a homogenisate of DOPE/TGMO-15/DOPE-PEG(5000) (76/20/4).

The invention claimed is:

1. A method for the conversion in an single heat cycle of at least 50% of lamellar particles in a dispersion of lamellar and optionally non-lamellar amphiphile particles to non-lamellar form, said method comprising
    forming a dispersion of lamellar and optionally non-lamellar particles comprising 0.5 to 20 wt % at least one amphiphilic structuring agent in an aqueous solution,
    heating said particles to a temperature between 80 and 150° C. and maintaining the temperature for a time of one minute to four hours,
    followed by cooling, wherein said non-lamellar particles have an internal region comprising a reversed cubic or hexagonal phase, L3 phase, or mixture thereof;
    wherein said lamellar particles have a solvent core region; and
    wherein, after cooling, at least 50% of said originally lamellar particles are converted to non-lamellar form.

2. A method as claimed in claim 1 wherein said heating and maintaining is to a temperature of between 80 to 150° C. and for a period of one minute to four hours, wherein said heating and maintaining is sufficient to provide a narrowing of said particle size distribution, after cooling, such that after cooling less than 1% of particles have a range outside of 0.05 to 1.5 µm.

3. A method as claimed in claim 1 wherein said heating and maintaining is to a temperature of between 80 to 150° C. and for a period of one minute to four hours, wherein said heating is sufficient to provide stabilization of said particle size distribution after cooling, such that the mean particle size after cooling increases no more than two-fold after at least 10 days at room temperature.

4. A method as claimed in claim 1 wherein said particles are colloidal.

5. A method as claimed claim 1 wherein said particles comprise at least 50% of a structure forming amphiphilic component "a", up to 40% of at least one structure swelling agent "b" and up to 20% of a dispersion stabilizing polymeric agent "c", wherein all parts are by weight relative to the total weight of a+b+c.

6. A method as claimed in claim 1 wherein said heating and maintaining is to a temperature of between 80 to 150° C. at which the equilibrium form of the particles is not non-lamellar.

7. A method as claimed in claim 6 wherein said heating and maintaining is to a temperature of between 80 to 150° C. at which the equilibrium form of the particles is L2 phase.

8. A method as claimed in claim 1 wherein said heating and maintaining is to a temperature of between 80 to 150° C. at which the equilibrium form of the particles is not liquid crystalline.

9. A method as claimed claim 1 wherein said dispersion of lamellar and/or non-lamellar particles is formed by sonication and/or extrusion.

10. A method as claimed in claim 1 further comprising drying the resultant non-lamellar particles formed after the cooling step, followed by resuspension/hydration of said particles.

11. A method as claimed in claim 1, wherein the duration of heating at a temperature of between 80 to 150° C. is for a period of from 2 to 30 minutes.

* * * * *